United States Patent
Fontanazzi et al.

(10) Patent No.: US 9,199,027 B2
(45) Date of Patent: Dec. 1, 2015

(54) APPARATUS FOR EXTRACORPOREAL BLOOD TREATMENT

(75) Inventors: Francesco Fontanazzi, Modena (IT); Alessandro Surace, Carpi (IT); Francesco Paolini, Ganaceto (IT)

(73) Assignee: Gambro Dasco S.P.A., Medolla (IT)

( * ) Notice: Subject to any disclaimer, the term of this patent is extended or adjusted under 35 U.S.C. 154(b) by 326 days.

(21) Appl. No.: 14/006,789

(22) PCT Filed: Mar. 20, 2012

(86) PCT No.: PCT/IB2012/000534
§ 371 (c)(1), (2), (4) Date: Dec. 3, 2013

(87) PCT Pub. No.: WO2012/172398
PCT Pub. Date: Dec. 20, 2012

(65) Prior Publication Data
US 2014/0088483 A1    Mar. 27, 2014

(30) Foreign Application Priority Data
Mar. 21, 2011  (IT) ............................. MI2011A0441

(51) Int. Cl.
*A61M 37/00* (2006.01)
*A61M 1/36* (2006.01)
*A61M 1/16* (2006.01)

(52) U.S. Cl.
CPC ............... *A61M 1/3639* (2013.01); *A61M 1/16* (2013.01)

(58) Field of Classification Search
CPC .............................. A61M 1/16; A61M 1/3639
USPC ........................................................ 604/5.04
See application file for complete search history.

(56) References Cited

U.S. PATENT DOCUMENTS

| | | | |
|---|---|---|---|
| 5,938,938 A | 8/1999 | Bosetto et al. | |
| 2005/0045540 A1 | 3/2005 | Connell et al. | |
| 2007/0108129 A1* | 5/2007 | Mori | A61M 1/16 210/646 |
| 2008/0217245 A1 | 9/2008 | Rambod et al. | |
| 2011/0098625 A1* | 4/2011 | Masala | A61M 1/342 604/6.09 |
| 2014/0323942 A1* | 10/2014 | Atallah | A61B 5/021 604/5.01 |

FOREIGN PATENT DOCUMENTS

| | | |
|---|---|---|
| EP | 778783 | 6/1997 |
| EP | 1 396 274 A1 | 3/2004 |
| WO | 97/02057 A1 | 1/1997 |
| WO | 2006/011009 A2 | 2/2006 |
| WO | 2010/004400 A2 | 1/2010 |

* cited by examiner

*Primary Examiner* — Leslie Deak
(74) *Attorney, Agent, or Firm* — K&L Gates LLP

(57) ABSTRACT

An apparatus for extracorporeal blood treatment is described, including a treatment unit, an extracorporeal blood circuit, an infusion line of a replacement fluid, a dialysis line connected in inlet to the second chamber, and a fluid evacuation line; sensors for determining a first parameter relating to a patient's blood volume (BV %) a second parameter relating to an ultrafiltration flow rate (UFR) or to a patient's weight loss rate (WLR), a third parameter (Cd, Na) relating to a conductivity or concentration of a liquid crossing the dialysis line and/or the infusion line, and a fourth parameter relating to an infusion flow rate ($Q_{INF}$), and a control unit for performing a control procedure.

20 Claims, 12 Drawing Sheets

APPARATUS FOR EXTRACORPOREAL BLOOD TREATMENT

CROSS RELATED APPLICATION

This application is the U.S. national phase of International Application No. PCT/IB2012/000534 filed 20 Mar. 2012 which designated the U.S. and claims priority to Italian Patent Application No. MI2011A000441 filed 21 Mar. 2011, the entire contents these applications are incorporated by reference.

The present invention relates to an apparatus for extracorporeal blood treatment.

Apparatus for extracorporeal blood treatment comprise at least one treatment unit (for example a dialyser or a filter or ultrafilter or a plasma filter or a filtering unit of another type) having a semipermeable membrane which separates the treatment unit into two chambers. An extracorporeal blood circuit enables circulation of blood removed from a patient internally of the first chamber. At the same time and typically in a counter-current direction with respect to the blood, a treatment fluid is made to circulate through an appropriate circuit in the second chamber of the treatment unit. This type of apparatus for blood treatment, known as dialysis apparatus, can be used for removal of excess solutes and fluids from the blood of patients suffering from kidney failure.

A particular type of apparatus for blood treatment, known as hemofiltration or hemodiafiltration apparatus, comprises the presence of an infusion line predisposed to sent a replacement fluid into the extracorporeal blood circuit. The infusion line or lines are connected upstream and/or downstream with respect to the treatment unit.

The above-described blood treatment apparatus can be controlled in various ways.

For example, the apparatus can be controlled volumetrically, such as to have predetermined flow rates along the various fluid transport lines.

Alternatively, the apparatus can be controlled such that the transmembrane pressure (herein indicated as TMP) follows a set value. Application WO2005IB01482 illustrates an apparatus and a process for setting the TMP value at a level which is such as to maximise the ultrafiltration flow rate and consequently the volume of fluid infused into the patient. This solution is advantageous as it maximises the flow rate of ultrafiltration and infusion, and thus maximises the convective exchange through the membrane and thus the purification of the blood from undesired particles.

Although the above-cited publication offers an advantageous procedure for setting TMP, extraction of fluid from a patient does not always correspond to a comfortable treatment for the patient.

Also known are technical solutions, for example described in patent document EP778783, in which the apparatus for blood treatment is controlled such that two parameters, i.e. the variation in blood volume and the weight loss rate are maintained in a range of acceptability by contemporaneously controlling the conductivity of the dialysis liquid (i.e. the fluid in inlet to the second chamber of the treatment unit) and the weight loss rate. Although this type of control has led to benefits for the patient subjected to treatment and has enabled two objectives to be reached during a single treatment, it should be noted that the use of the method of document EP778783 has essentially been limited to apparatus for hemodialysis and thus has poor convective exchange capacity.

SUMMARY

An aim of the present invention is to make available an apparatus for blood treatment which is able to operate efficiently even in the presence of high convective exchange, i.e. in the presence of infusion lines for infusing relatively high quantities of replacement fluid during treatment and guaranteeing at the same time a high degree of patient comfort.

A further aim of the present invention is to make available an apparatus which is able to control convective exchange and contemporaneously also control weight loss and plasma conductivity and sodium concentration, to be delivered to the patient under treatment.

An additional aim of the present invention is to provide an apparatus which is able to determine a setting value of TMP in a way which is simple and rapid and which is capable, if possible, of increasing the volume of liquid exchanged with the patient, while avoiding conflicts with any other controls aimed at improving the comfort of the patient during treatment.

A further aim of the invention is to provide an apparatus which, though accelerating the search sequence for the TMP setting, is however able to operate safely.

At least one of the above-indicated aims is substantially attained by an apparatus for blood treatment as in one or more of the appended claims.

Some aspects of the invention are now described.

In a $1^{st}$ aspect, an apparatus for extracorporeal blood treatment comprises: at least one treatment unit, having at least one first chamber and at least one second chamber, separated from one another by a semipermeable membrane, at least one blood removal line connected to an inlet port of the first chamber and predisposed to remove blood from a patient, at least one blood return line connected with an outlet port of the first chamber and predisposed to return treated blood to the patient (the blood removal line, the blood return line and the first chamber being part of an extracorporeal blood circuit), at least one infusion line of a replacement fluid connected with the extracorporeal circuit or directly connectable with a patient and, optionally, a dialysis line connected in inlet to the second chamber, at least one fluid evacuation line connected to an outlet port of the second chamber, and sensor means.

The sensor means are positioned and configured such as to determine:
- a first parameter relating to a blood volume BV % of the patient;
- at least one second parameter relating to a parameter selected from among a group comprising: an ultrafiltration flow rate UFR through the membrane, a weight loss rate WLR of the patient, and an accumulated weight loss WL;
- a third parameter Cd, Na relating to a conductivity of a liquid crossing the dialysis line and/or the infusion line or at a concentration in sodium or another predetermined substance of the liquid crossing the dialysis line and/or the infusion line; and
- a fourth parameter relating to an infusion flow rate $Q_{INF}$ of the replacement fluid crossing the infusion line.

The apparatus further comprises a control unit connected with the sensor means and configured such as to perform a control procedure comprising:
- receiving, from the sensor means, measured values of the parameters, and
- calculating, using the measured values and the prescription values of the variation in blood volume BV %$_{target}$, the target weight loss WL$_{target}$, of the plasma conductivity or sodium concentration C$_{target}$, Na$_{target}$, and the infusion volume V$_{INFtarget}$ to be reached in the patient in a predetermined treatment time, the following control values to be set during a time interval after the instant in which the control is made: a conductivity or sodium concentration value $Cd_{(t)}$; $Na_{(t)}$ of the liquid crossing the dialysis line and/or the infusion line; a weight loss rate value $WLR_{(t)}$, and an infusion rate value $Q_{INF(t)}$.

A 2nd aspect comprises an apparatus for extracorporeal blood treatment comprising:

at least one treatment unit having at least one first chamber and at least one second chamber, separated from one another by a semipermeable membrane, at least one blood removal line connected to an inlet port of the first chamber and predisposed to remove blood from a patient, at least one blood return line connected to an outlet port of the first chamber and predisposed to return treated blood to the patient (the blood removal line, the blood return line and the first chamber being part of an extracorporeal blood circuit), at least one infusion line of a replacement fluid connected to the extracorporeal circuit or directly connectable with a patient and, optionally, a dialysis line connected in inlet to the second chamber, at least one fluid evacuation line connected with an outlet port of the second chamber, and sensor means. The sensor means are positioned and configured such as to determine:

a first parameter relating to a blood volume BV % of the patient;

at least one second parameter relating to one value selected from among a group comprising: an ultrafiltration rate UFR through the membrane, a weight loss rate WLR of the patient, and an accumulated weight loss WL;

a third parameter Cd, Na relating to a conductivity of a liquid crossing the dialysis line and/or the infusion line or to a sodium concentration or another predetermined substance of the liquid crossing the dialysis line and/or the infusion line; and a fourth parameter relating to a transmembrane pressure TMP between the first and second chamber.

The apparatus further comprises a control unit connected to the sensor means and configured such as to perform a control procedure comprising:

receiving measured values of the parameters from the sensor means, and calculating, on the basis of the measured values and the prescription values of the variation of blood volume BV $\%_{target}$, the weight loss $WL_{target}$, the plasma conductivity or sodium concentration $C_{target}$, $Na_{target}$ to be reached in the patient in a predetermined treatment time as well as the transmembrane pressure value $TMP_{target}$ to be followed during a predetermined treatment time, the following control values to set during a time interval that is subsequent to the instant of control: a conductivity or sodium concentration value $Cd_{(t)}$, $Na_{(t)}$ of the liquid crossing the dialysis line and/or the infusion line, a weight loss rate $WLR_{(t)}$, and a transmembrane pressure value $TMP_{(t)}$.

In a 3rd aspect in accordance with any one of the preceding aspects, the control procedure comprises setting the control values during a time interval $\Delta t$ subsequent to the control instant t.

In a 4th aspect in accordance with any one of the preceding aspects, the control unit is configured or programmed such as to repeat the control procedure at control instants t which are temporally consecutive of one another.

In a 5th aspect in accordance with any one of the preceding aspects, the control values are calculated on the basis of:

measured values where the fourth parameter is the infusion rate, and prescription values of the blood volume variation BV $\%_{target}$, of the weight loss $WL_{target}$, of the plasma conductivity or sodium concentration $C_{target}$, $Na_{target}$, of the infusion volume $V_{INFtarget}$ to be reached in the patient in a predetermined treatment time.

In a 6th aspect, in accordance with any one of the preceding aspects from the first to the fourth, the control values are calculated on the basis of:

measured values where the fourth parameter is the transmembrane pressure and prescription values of the blood volume variation BV $\%_{target}$, of the weight loss $WL_{target}$, of the plasma conductivity or sodium concentration $C_{target}$ to be reached in the patient in a predetermined treatment time, and of the transmembrane pressure $TMP_{target}$, predetermined or calculated, to be followed during the predetermined treatment time.

In a 7th aspect in accordance with any one of the preceding aspects, the control values are also calculated on the basis of a prescription value of a volume to be infused in the patient $V_{INFtarget}$ by the end of treatment.

In an 8th aspect in accordance with any one of the preceding aspects, the control values are also calculated on the basis of a prescription flow rate of a volume to be infused in the patient $Q_{INFtarget}$ during the treatment.

In a 9th aspect in accordance with any one of the preceding aspects, the apparatus comprises a first regulating device for regulating an ultrafiltration rate or a transmembrane pressure between the first and the second chamber of the treatment unit, the first regulating device being connected to the control unit and being active on at least one of the extracorporeal blood circuit and fluid evacuation line.

In a 10th aspect, in accordance with any one of the preceding aspects, the apparatus comprises a second regulating device for regulating a composition of the dialysis liquid and/or the replacement liquid, the second regulating device being connected to the control unit and being active on the dialysis line and/or on the infusion line for regulating the conductivity or sodium concentration Cd, Na of the liquid crossing the dialysis line and/or the infusion line.

In an 11th aspect in accordance with any one of the preceding aspects, the step of setting the control values during the procedure comprises:

commanding the second regulating device such as to impose the control value relating to the conductivity or sodium concentration $Cd_{(t)}$, $Na_{(t)}$ on the liquid crossing the dialysis line and/or the infusion line; and commanding the first regulating device to impose the control value relating to the weight loss rate $WLR_{(t)}$.

In a 12th aspect in accordance with any one of the preceding aspects, the apparatus comprises at least one infusion pump, or another regulating device of the fluid flow along the infusion line or lines, active on the infusion line and connected to the control unit for causing an infusion liquid flow along the line and wherein the control unit is configured such as to control the infusion pump and the first regulating device such as to impose both the control value relating to the weight loss rate $WLR_{(t)}$ and the control value relating to the infusion line $Q_{INF(t)}$. The regulation of the infusion rate, especially if concerned with a replacement fluid line located upstream of the treatment unit, can also be regulated in accordance with the transmembrane pressure membrane $TMP_{(t)}$.

In a 13th aspect in accordance with any one of the preceding aspects, the control unit is configured such as to command the second regulating device in order to impose the control parameter relating to the conductivity or sodium concentration $Cd_{(t)}$, $Na_{(t)}$ and to the liquid crossing the dialysis line and the liquid crossing the infusion line.

In a 14th aspect in accordance with any one of the preceding aspects, in which the control procedure uses a mathematical model M, representing kinetics of the solutes in a distribution volume in the patient, in order to determine an equivalent sodium concentration value $Na_{eq(t)}$ at the control instant t, the model being memorised in a memory associated to the control unit, the control unit being configured such as to apply the following values in inlet to the mathematical model:

a value of the equivalent sodium concentration relative to a preceding control instant $Na_{eq(t-\Delta t)}$, a control value of the conductivity or the sodium concentration of the dialysis liquid at a preceding control instant $Cd_{(t-\Delta t)}$, $Na_{t-\Delta t}$, at least one selected value from the group comprising: a control value relating to the ultrafiltration flow at a preceding control instant $UFR_{(t-\Delta t)}$, a control value relating to the weight loss rate up to the preceding control instant $WLR_{(t-\Delta t)}$, an accumulated weight loss value at control instant $WL_{(t)}$, a total convective and diffusive clearance value measured at the control instant $Cl_{mes(t)}$ or an estimated total convective and diffusive clearance parameter $Cl_{mes(t)}$, a reference value relating to a volume V of distribution of solutes in the patient or a body water volume TBW. The distribution volume V is determined for each patient on the basis of the weight loss target $WL_{target}$, the total accumulated weight loss $WL_{(t)}$ and the body weight volume TBW; the last of these is estimated as described herein below (example formulae for V and TWL are provided in the detailed description);

and for receiving, in outlet from the mathematical model, a value of an equivalent sodium concentration $Na_{eq(t)}$ at the control instant t.

Note that by equivalent sodium concentration at instant t ($Na_{eq(t)}$) reference is made to the constant sodium concentration in the dialysis liquid that, if applied at the start of treatment up to a certain instant t, would lead to the same plasma sodium concentration in the patient as is obtained at the same instant t with the variation of sodium concentration or conductivity set by the control procedure up to time t.

In a 15$^{th}$ aspect, in accordance with the preceding aspect, an estimated total convective and diffusive clearance value $Cl_{mes(t)}$ is calculated on the basis of a current measured value of the infusion flow rate $Q_{INFmes(t)}$ and one from among current measured value of blood flow $Q_{Bmes(t)}$ and a current diffusive clearance value $Cl_{diff(t)}$. Alternatively the estimated total convective and diffusive clearance value $Cl_{mes(t)}$ can be mathematically extrapolated from preceding values assumed by Cl.

In a 16$^{th}$ aspect in accordance with the 14$^{th}$ or 15$^{th}$ aspect, the mathematical model is representative of a kinetics of the solutes in a distribution volume in the patient, optionally according to a single-compartment model.

In a 17$^{th}$ aspect in accordance with the 14$^{th}$ or 15$^{th}$ or 16$^{th}$ aspect of the control procedure comprises also using the equivalent sodium concentration parameter at the instant t (i.e. $Na_{eq(t)}$) for determining the control values.

In an 18$^{th}$ aspect in accordance with any one of the preceding aspects, the control procedure comprises the following sub-steps:

receiving the prescription values of the changes in blood volume $BV \%_{target}$, the weight loss $WL_{target}$ and the plasma conductivity or sodium concentration of $C_{target}$, $Na_{target}$ to be reached at end of treatment;

receiving a treatment time value T;

determining, on the basis of the prescription values and the treatment time value T, respective target parameters which describe the desired progress over time of the variation in blood volume $BV \%_{target(t)}$, of the weight loss $WL_{target(t)}$, $WLR_{target(t)}$ and the equivalent sodium concentration $Na_{eq\text{-}target(t)}$.

In a 19$^{th}$ aspect, in accordance with the preceding aspect in which the control procedure comprises the sub-steps of:

determining at least one first error parameter $ERR\_BV\_UF_{(t)}$ on the basis of:

the difference between the measured value of the first parameter $BV \%_{mes(t)}$ at the control instant t and a corresponding value on the target profile relating to the variation in blood volume in time $BV \%_{target(t)}$ and the difference between a measured value of weight loss or the weight loss rate $WL_{mes(t)}$;

$WLR_{mes(t)}$ at the control instant t and a corresponding value given by the target profile relating to weight loss or weight loss rate $WL_{target(t)}$; $WLR_{target(t)}$ over time; and determining at least one second error parameter $ERR\_BV\_Na_{(t)}$ on the basis of:

the difference between the value of the equivalent sodium parameter $Na_{eq(t)}$ at control instant t and a corresponding parameter on the target profile relating to the variation over time of the equivalent sodium concentration $Na_{eq\text{-}target(t)}$; and the difference between the measured value of the first parameter $BV \%_{mes(t)}$ at the control instant t and the corresponding value on the target profile relating to the variation in blood volume over time $BV \%_{target(t)}$.

In a 20$^{th}$ aspect in accordance with the preceding aspect, the control sodium conductivity or concentration value $Cd_{(t)}$, $Na_{(t)}$ to impose on the liquid crossing the dialysis line and/or the infusion line is calculated on the basis of the second error parameter $ERR\_BV\_Na_{(t)}$ and on the basis of the conductivity or sodium concentration value $Cd_{(t-\Delta t)}$, $Na_{(t-\Delta t)}$ relating to the preceding control instant.

In a 21$^{st}$ aspect in accordance with the 19$^{th}$ or 20$^{th}$ aspect, the control flow rate value to be imposed for the weight loss rate $WLR_{(t)}$ is calculated on the basis of the first error parameter $ERR\_BV\_UF_{(t)}$ and on the basis of the ultrafiltration flow rate $UFR_{(t-\Delta t)}$ relating to the preceding control instant.

In a 22$^{nd}$ aspect in accordance with any one of the preceding aspects, the control unit is configured for:

comparing the measured value of the first parameter $BV \%_{mes(t)}$ with a reference threshold, verifying whether the measured value of the first parameter falls below the threshold, and commanding infusion of a bolus of a predetermined volume of replacement liquid through the infusion line if the verification gives a positive result.

In a 23$^{rd}$ aspect in accordance with the preceding aspect, commanding the infusion of the bolus comprises imposing a predetermined flow for a predetermined time of administration to the infusion pump.

In a 24$^{th}$ aspect in accordance with the 22$^{nd}$ or 23$^{rd}$ aspect the control unit is configured for setting, during administration of the bolus, an ultrafiltration flow rate value of zero.

In a 25$^{th}$ aspect in accordance with the 23$^{rd}$ or 24$^{th}$ aspect, wherein commanding the infusion of the bolus comprises commanding, during administration of the bolus, the second regulating device of the liquid composition such as to impose a predetermined value on the conductivity or sodium concentration $Cd_{(t)}$, $Na_{(t)}$ on the liquid crossing the infusion line.

In a 26$^{th}$ aspect in accordance with any one of the preceding aspects, the sensor means comprise at least one first sensor S7 acting on the extracorporeal circuit for detecting the variation $BV \%$ of the blood volume of the patient.

In a 27$^{th}$ aspect in accordance with any one of the preceding aspects, the sensor means comprise at least one second sensor S6 active on the evacuation line for determining the ultrafiltration rate UFR across the membrane, or the weight loss rate WLR of the patient, or an accumulated weight loss WL.

In a 28$^{th}$ aspect in accordance with any one of the preceding aspects, the sensor means comprise at least one third sensor S8 active on the dialysis line or on the infusion line or on a common supply line of the dialysis line and the infusion line, the third sensor being a conductivity or concentration sensor predisposed for determining the conductivity of a liquid crossing the dialysis line and/or the infusion line or the sodium concentration of the liquid crossing the dialysis line and/or the infusion line.

In a 29$^{th}$ aspect in accordance with any one of the preceding aspects, the sensor means comprise at least one fourth sensor S5 for determining an infusion rate $Q_{INF}$ of the replacement fluid crossing the infusion line and at least one fifth pressure sensor S1, S2, S3, S4 for determining a transmembrane pressure TMP between the first and the second chamber.

A 30$^{th}$ aspect concerns an apparatus for extracorporeal blood treatment comprising at least one treatment unit having at least one first chamber and at least one second chamber separated from one another by a semipermeable membrane; at least one blood removal line connected to an inlet port of the first chamber and predisposed for removing blood from a patient; at least one blood return line connected with an outlet port of the first chamber and predisposed to return treated blood to the patient. The blood removal line, the blood return line and the first chamber are part of an extracorporeal blood circuit of the apparatus. The apparatus also exhibits at least one infusion line of a replacement fluid connected with the extracorporeal circuit or directly connectable to a patient;

at least one dialysis line connected in inlet to the second chamber; at least one fluid evacuation line connected with an outlet port of the second chamber; and sensor means for determining:
a first parameter relating to a blood volume BV % of the patient;
at least a second and a third parameter selected from among: an ultrafiltration flow rate UFR across the membrane, a weight loss rate WLR of the patient (note that the weight loss rate can be derived from the accumulated weight loss WL divided by a time interval), an infusion rate $Q_{INF}$ of the replacement fluid crossing the infusion line;
a fourth parameter relating to a transmembrane pressure TMP between the first and the second chamber.

Further, the apparatus comprises a first regulating device active on at least one of the extracorporeal circuit and the fluid evacuation line and configured such as to regulate an ultrafiltration flow rate UFR or a transmembrane pressure TMP between the first and the second chamber of the treatment unit, and a control unit connected with the sensor means and with the first regulating device and configured such as to perform a control procedure in order to regulate the weight loss rate and at least one setting sequence for maximising the convective exchange across the semipermeable membrane.

In a 31$^{st}$ aspect, in accordance with the 30$^{th}$ aspect the control unit is programmed or configured such as to perform, at least at a control instant t, a control procedure comprising:
receiving from the sensor means measured values of the first parameter BV %$_{mes(t)}$ and the second and third parameter UFR$_{mes(t)}$, WLR$_{mes(t)}$, $Q_{INFmes(t)}$, and
calculating, on the basis of the measured values of at least one prescription value of the blood volume variation BV %$_{target}$, a control value relating to the weight loss rate WLR$_{(t)}$ that the apparatus must impose,
imposing the control value WLR$_{(t)}$ on the weight loss rate.

In a 32$^{nd}$ aspect according to the 30$^{th}$ or the 31$^{st}$ aspects, the control unit is further programmed or configured such as to perform at least one setting instant τ and a setting sequence of the transmembrane pressure, the setting sequence comprising:
imposing on a first value of the transmembrane pressure TMP$_n$ a first increase δTMP$_n$ such as to reach a second transmembrane pressure value TMP$_{n+1}$;
determining a variation ΔUFR$_{(n)}$ between the ultrafiltration flow across the membrane at the first transmembrane pressure TMP$_n$ and the ultrafiltration flow at the second transmembrane pressure value TMP$_{n+1}$, in which the variation in ultrafiltration flow rate is determined either by direct measuring of the ultrafiltration flow or indirectly, taking into account both the replacement liquid flow variation ΔQ$_{INF(n)}$ along the infusion line and the variations in weight loss rate ΔWLR$_{(n)}$ due to the control procedure;
comparing the ultrafiltration variation ΔUFR$_{(n)}$ with a reference value and, if the value of the variation ΔUFR$_{(n)}$ is greater than the reference value, commanding the first regulation device, imposing a second increase δTMP$_{n+1}$ on the second transmembrane pressure in order to reach a third value of the transmembrane pressure value TMP$_{n+2}$.

In a 33$^{rd}$ aspect according to any one of aspects from the 30$^{th}$ to the 32$^{nd}$, the sensor means are predisposed to determine at least one fifth parameter Cd, Na relating to a conductivity of a liquid crossing the dialysis line and/or the infusion line or at a sodium concentration (or a predetermined other substance to be monitored) of the liquid crossing the dialysis line and/or the infusion line.

In a 34$^{th}$ aspect according to any one of aspects from the 30$^{th}$ to the 33$^{rd}$, in the control procedure the step of receiving comprises receiving, from the sensor means, measured values of the:
first parameter BV %$_{mes(t)}$,
second parameter UFR$_{mes(t)}$, WLR$_{mes(t)}$ comprising the ultrafiltration flow rate UFR across the membrane or the weight loss rate WLR of the patient,
the third parameter Q$_{INF\,mes(t)}$ comprising the infusion flow rate $Q_{INF}$ of the replacement fluid crossing the infusion line, and/or the fourth parameter TMP$_{mes(t)}$ and
the fifth parameter Cd$_{mes(t)}$, Na$_{mes(t)}$.

In a 35$^{th}$ aspect according to any one of aspects from the 30$^{th}$ to the 34$^{th}$, the control procedure includes that the step of calculating comprises calculating, in accordance with the measured values and prescription values of variation of blood volume BV %$_{target}$, of the weight loss WL$_{target}$ and the plasma conductivity or sodium concentration in the patient (or alternatively the infusion volume V$_{INFtarget}$ of a transmembrane pressure value TMP$_{target}$ to be followed in a predetermined treatment time), the following control values: get to
a conductivity or sodium concentration value Cd$_{(t)}$; Na$_{(t)}$ of the liquid crossing the dialysis line and/or the infusion line; and
a value of weight loss rate WLR$_{(t)}$.

In a 36$^{th}$ aspect according to any one of aspects from the 30$^{th}$ to the 35$^{th}$, the control procedure comprises that the step of imposing comprises imposing the control value relating to the conductivity or sodium concentration Cd$_{(t)}$, Na$_{(t)}$ and the value relating to the weight loss rate WLR$_{(t)}$.

In a 37$^{th}$ aspect according to any one of aspects from the 30$^{th}$ to the 36$^{th}$, the control unit is configured such as to perform the control procedure at a plurality of control instants t that are temporally reciprocally successive.

In a 38$^{th}$ aspect according to any one of aspects from the 30$^{th}$ to the 37$^{th}$, the control unit is configured such as to impose the control values during a time interval Δt after each control instant t.

In a 39$^{th}$ aspect according to any one of aspects from the 30$^{th}$ to the 38$^{th}$, the control unit is configured such as cyclically to repeat the control procedure during the whole treatment.

In a 40$^{th}$ aspect according to any one of aspects from the 30$^{th}$ to the 39$^{th}$, the control unit is configured such as to perform the setting sequence at a plurality of setting instants τ temporally successive to one another, and wherein the control unit is configured such as to perform the control procedure at more frequent control instants with respect to the setting instants in which the setting sequence is performed.

In a 41$^{st}$ aspect according to any one of aspects from the 30$^{th}$ to the 40$^{th}$, the setting sequence comprises:

repeating n times the step of increasing the transmembrane pressure by commanding the first regulating device, determining whether the ultrafiltration flow rate variation ΔUFR$_n$ corresponding to each n$^{th}$ transmembrane pressure increase is greater that the respective reference value; and either determining an (n+1)$^{th}$ increase δTMP$_{n+1}$ if the ultrafiltration flow rate variation at the nth transmembrane pressure increase ΔUFR$_n$ is greater than the respective reference value, or, vice-versa terminating the setting sequence and imposing the n$^{th}$ pressure value TMP$_n$ as the setting value of the transmembrane pressure, if the ultrafiltration flow variation ΔUFR$_n$ corresponding to the n$^{th}$ transmembrane pressure increase is lower than the reference value.

In a 42$^{nd}$ aspect, in accordance with the preceding aspect in which the setting value is successively reduced by a predetermined safety margin.

In a 43$^{rd}$ aspect in accordance with any one of the 41$^{st}$ or the 42$^{nd}$ aspects wherein the (n+1)$^{th}$ increase δTMP$_{n+1}$ is of a greater entity than the nth increase δTMP$_n$.

In a 44$^{th}$ aspect according to any one of the 41$^{st}$, 42$^{nd}$ or 43$^{rd}$ aspects, the control unit is configured such as to calculate an (n+1)$^{th}$ increase δTMP$_{n+1}$ as a function of the ultrafiltration flow rate variation ΔUFR$_n$ corresponding to the nth transmembrane pressure increase δTMP$_n$ and the value of the n$^{th}$ transmembrane pressure increase δTMP$_n$.

In a 45$^{th}$ aspect in accordance with any one of the 41$^{st}$ or 42$^{nd}$ or 43$^{rd}$ aspects, the control unit is configured to calculate an (n+1)$^{th}$ increase δTMP$_{n+1}$ as a function of the ultrafiltration blood flow variation ΔUFR$_n$ corresponding to the nth transmembrane pressure increase δTMP$_n$ and the value of the n$^{th}$ transmembrane pressure increase δTMP$_n$ using the formula:

$$\delta TMP_{n+1} = (\Delta UFR_n) \cdot (K)$$

where:

K is the relation between the value of the n$^{th}$ transmembrane pressure increase (δTMP$_n$) and the value of a correction factor, optionally wherein the value of the correction factor is selected from among the group comprising:

a prefixed value, a mathematical function of the reference value, a mathematical function of a treatment mode at which the apparatus has been set, a mathematical function of a treatment mode at which the apparatus has been set and of the reference value.

In a 46$^{th}$ aspect in accordance with any one of the preceding aspects, the apparatus comprises at least one user interface, connected to the control unit, the user interface being configured such as to receive command signals entered by a user via the user interface.

In a 47$^{th}$ aspect in accordance with the preceding aspect, the control unit is configured such as to receive a start command of the setting sequence and/or the control procedure following a command that can be entered by a user acting on a manual activation element of the interface.

In a 48$^{th}$ aspect according to the 46$^{th}$ aspect, the control unit is configured to start the sequence and/or the procedure automatically.

In a 49$^{th}$ aspect in accordance with any one of aspects from the 30$^{th}$ to the 48$^{th}$ aspects, the control unit is programmed to:

measure a time that has passed from a start of treatment of a patient, automatically activate a first setting sequence after a first time interval T$_1$ from the start of treatment, measure a time that has passed since the end of the first setting sequence, automatically activate a second setting sequence that has passed since a second time interval T$_2$ from the end of the first setting sequence, activate any further setting sequence that has passed since a time interval T$_n$ since the end of a preceding setting sequence.

In a 50$^{th}$ aspect, in accordance with the preceding aspect the duration of the time intervals T$_1$, T$_2$, T$_n$ is not uniform, optionally in which the duration of each time interval subsequent to the first is greater than the duration of a time interval preceding it.

In a 51$^{st}$ aspect, in accordance with any of the aspects from the 30$^{th}$ to the 50$^{th}$, the control unit is programmed such that during the setting sequence, following each command for increase of the transmembrane pressure, a time transitory T$_r$ is included before performing a subsequent increase in transmembrane pressure.

In a 52$^{nd}$ aspect, in accordance with the preceding aspect, the duration of the time transitory T$_r$ is not uniform.

In a 53$^{rd}$ aspect according to any one of the aspects from the 30$^{th}$ to the 52$^{nd}$, the control unit, during the sequence, is predisposed to verify whether between a pressure increase and the successive one there has been a variation in weight loss rate ΔWLR imposed by the control procedure and, if the response is affirmative, to prolong the duration of the time transitory T$_r$ such that at least one predetermined auxiliary time delay has passed since the last weight loss rate variation.

In a 54$^{th}$ aspect in accordance with any one of aspects from the 30$^{th}$ to the 53$^{rd}$, the control unit is predisposed to verify whether between a pressure increase and a next pressure increase there has been a variation in the weight loss rate ΔWLR imposed by the control procedure and, if the response is affirmative, the control unit is programmed to prolong a duration of a time transitory T$_r$ between a transmembrane pressure increase and a following transmembrane pressure increase, such that at least one predetermined auxiliary temporal delay has passed since the last weight loss rate variation before effecting a new pressure increase.

In a 55$^{th}$ aspect, in accordance with the preceding aspect the auxiliary temporal delay being less than a temporal delay between a control procedure and a next control procedure.

In a 56$^{th}$ aspect according to any one of aspects from the 51$^{st}$ to the 55$^{th}$, the control unit is predisposed to calculate the time transitory T$_r$ as a function of the pressure increase between a transmembrane pressure value TMP$_n$ and a next TMP$_{n+1}$.

In a 57$^{th}$ aspect in accordance with any one of aspects from the 51$^{st}$ to the 55$^{th}$, the control unit is predisposed to calculate the time transitory $T_r$ as a function of the variation of the weight loss rate $\Delta WLR$ imposed by the control procedure between a pressure increase and a next pressure increase.

In a 58$^{th}$ aspect, in accordance with any one of aspects from the 51$^{st}$ to the 57$^{th}$, the control unit is programmed such that during the setting sequence each step of comparison of the value of the ultrafiltration flow rate variation $\Delta UFR_1$; $\Delta UFR_n$ with a respective reference value $\Delta UFR_{ref}$ is performed after the time transitory $T_r$, with the aim of enabling a stabilising of the value of the ultrafiltration flow variation.

In a 59$^{th}$ aspect in accordance with any one of aspects from the 30t$^h$ to the 58$^{th}$, during the setting sequence the control unit is configured such as to determine the variation of the ultrafiltration flow rate variation $\Delta UFR_{(n)}$ between a transmembrane pressure variation $\delta TMP_n$ and a next $\delta TMP_{n+1}$ as a sum of the replacement liquid flow rate variation along the infusion line $\Delta Q_{INF(n)}$ and the weight loss rate $\Delta WLR_{(n)}$ that have been verified and measured in a time duration between the transmembrane pressure variation $\delta TMP_n$ and the next $\delta TMP_{n+1}$.

In a 60$^{th}$ aspect, according to any one of aspects from the 30$^{th}$ to the 59$^{th}$, the control value or values are also calculated in accordance with a measured value of replacement fluid flow rate $Q_{INFmes(t)}$ along the infusion line.

In a 61$^{st}$ aspect in accordance with any one of the preceding aspects from the 30$^{th}$ to the 60$^{th}$, the control values are calculated also in accordance with a prescription value of volume to be infused in the patient $V_{INFtarget}$ by end of treatment.

In a 62$^{nd}$ aspect in accordance with any one of the preceding aspects from the 30$^{th}$ to the 60$^{th}$, the control values are calculated also in accordance with a prescription value of flow rate to be infused in the patient $Q_{INFtarget}$ during treatment.

In a 63$^{rd}$ aspect in accordance with any one of the preceding aspects from the 30$^{th}$ to the 62$^{nd}$, the apparatus comprises a first regulating device for regulating the ultrafiltration or transmembrane pressure between the first and the second chamber of the treatment unit, the first regulating device being connected to the control unit and being active on at least one of the extracorporeal circuit and the fluid evacuation line.

In a 64$^{th}$ aspect in accordance with any one of the preceding claims from the 30$^{th}$ to the 63$^{rd}$, the apparatus comprises a second regulating device for regulating a composition of the dialysis liquid and/or the replacement liquid, the second regulating device being connected to the control unit and being active on the dialysis line and/or the infusion line such as to regulate the sodium conductivity or concentration Cd, Na of the liquid crossing the dialysis line and/or the infusion line.

In a 65$^{th}$ aspect in accordance with any one of the preceding aspects from the 30$^{th}$ to the 64$^{1h}$, the step of imposing the control values during the procedure comprises:

commanding the second regulating device such as to impose the control value relating to the conductivity or the sodium concentration $Cd_{(t)}$, $Na_{(t)}$ on the liquid crossing the dialysis line and/or the infusion line; and commanding the first regulating device in order to impose the control value relating to the weight loss rate $WLR_{(t)}$.

In a 66$^{th}$ aspect in accordance with any one of the preceding aspects from the 30$^{th}$ to the 65$^{th}$, the apparatus comprises at least one infusion pump active on the infusion line and connected to the control unit such as to cause an infusion liquid flow rate along the line and wherein the control unit is configured such as to control the infusion pump and the first regulating device such as to impose both the control value relating to the weight loss rate $WLR_{(t)}$ and the control value relating to the infusion flow rate $Q_{INF(t)}$ or the transmembrane pressure $TMP_{(t)}$.

In a 67$^{th}$ aspect, in accordance with any one of the preceding aspects from the 30$^{th}$ to the 66$^{th}$, the control unit is configured to command the second regulating device to impose the same control value relating to the sodium conductivity or concentration $Cd_{(t)}$, $Na_{(t)}$ and on the liquid crossing the dialysis line and the liquid crossing the infusion line.

In a 68th aspect in accordance with any one of the preceding aspects from the 30th to the 67th, the control procedure uses a mathematic model M, representing a kinetics of the solutes in a distribution volume in the patient, in order to determine a value of an equivalent sodium concentration $Na_{eq(t)}$ at the control instant t, the model being memorised in a memory associated to the control unit, the control unit being configured such as to apply the following values in input to the mathematical model:

a value of the equivalent sodium concentration relative to a preceding control instant $Na_{eq(t-\Delta t)}$, a control value of the conductivity or the sodium concentration of the dialysis liquid at a preceding control instant $Cd_{(t-\Delta t)}$, $Na_{(t-\Delta t)}$, at least one value selected from among a group comprising: a control value relating to the ultrafiltration flow rate at a preceding control instant $UFR_{(t-\Delta t)}$, a control value relating to the weight loss rate at a preceding control instant $WLR_{(t-\Delta t)}$, an accumulated weight loss value up to a control instant $WL_{(t)}$, a total convective and diffusive clearance value measured at the control instant $Cl_{mes(t)}$ or a total convective and diffusive clearance value $Cl_{mes(t)}$;

a reference value relating to a distribution volume V of solutes in the patient or corporeal water volume TBW. The distribution volume V is determined for each patient on the basis of the weight loss objective $WL_{target}$, the total accumulated weight loss $WL_{(t)}$ and the volume of corporeal water volume TBW; the last is estimated as described herein below (example formulae for V and TWL are provided in the detailed description);

and to receive in output from the mathematical model the value of an equivalent sodium concentration $Na_{eq(t)}$ at the control instant t.

It should be noted that by equivalent sodium concentration at instant t ($Na_{eq(t)}$) what is intended is the constant sodium concentration in the dialysis liquid which, if it were applied at the start of treatment up to a certain instant t, would lead to the same plasma sodium concentration in the patient as is obtained at the same instant t with the variation in sodium concentration or conductivity imposed by the control procedure up to time t.

In a 69$^{th}$ aspect in accordance with the preceding aspect the estimated total convective and diffusive clearance value $Cl_{mes(t)}$ is calculated on the basis of a current measured value of the infusion rate $Q_{INFmes(t)}$ and of one from between a current measured value of blood flow $Q_{Bmes(t)}$ and a current diffusive clearance value $Cl_{diff(t)}$. Alternatively, the estimated total convective and diffusive clearance value $Cl_{mes(t)}$ can be mathematically extrapolated from preceding assumed values from C1.

In a 70$^{th}$ aspect in accordance with the 68$^{th}$ or 69$^{th}$ aspects, the mathematical model is representative of a kinetics of the solutes in a distribution volume in the patient, optionally according to a single-compartment model.

In a 71$^{st}$ aspect, in accordance with the 68$^{th}$, 69$^{th}$ or 70$^{th}$ aspects, the control procedure comprises also using the equivalent sodium concentration value at the instant t (i.e. $Na_{eq(t)}$) for the determination of the control values.

In a 72$^{nd}$ aspect, in accordance with any one of the preceding aspects from the 30$^{th}$ to the 71$^{st}$, the control procedure comprises the following sub-steps:

receiving the prescription values of the blood volume variation BV %$_{target}$, the weight loss WL$_{target}$ and the plasma conductivity or sodium concentration C$_{target}$, Na$_{target}$ to be reached at end of treatment;

receiving a treatment time value T;

determining, on the basis of the prescription values and the treatment time value T respective target profiles which describe the desired temporal progression of the blood volume variation BV %$_{target(t)}$, of the weight loss or the weight loss rate WL$_{target(t)}$, WLR$_{target(t)}$ and of the equivalent sodium concentration Na$_{eq\text{-}target(t)}$.

In a 73$^{rd}$ aspect in accordance with the preceding aspect, the control procedure comprises the sub-steps of:

determining at least one first error parameter ERR_BV_UF$_{(t)}$ on the basis of:

the difference between the measured value of the first parameter BV %$_{mes(t)}$ at the control instant t and a corresponding value on the target profile relating to the variation in blood volume over the time BV %$_{target(t)}$ and the difference between a measured value of the weight loss or the weight loss rate WL$_{mes(t)}$;

WLR$_{mes(t)}$ at the control instant t and a corresponding value given by the target profile relating to the weight loss or the weight loss rate WL$_{target(t)}$; WLR$_{target(t)}$ over the time; and determining at least one second error parameter ERR_BV_Na$_{(t)}$ on the basis of:

the difference between the value of the equivalent sodium concentration Na$_{eq(t)}$ at the control instant t and a corresponding value on the target profile relating to the variation over the time of the equivalent sodium concentration Na$_{eq\text{-}target(t)}$, and the difference between the measured value of the first parameter BV %$_{mes(t)}$ at the control instant t and the corresponding value on the target profile on variation of the blood volume in time BV %$_{target(t)}$.

In a 74$^{th}$ aspect, in accordance with the preceding aspect, the control conductivity or sodium concentration Cd$_{(t)}$, Na$_{(t)}$ to be imposed on the liquid crossing the dialysis line and/or the infusion line is calculated as a function of the second error parameter ERR_BV_Na$_{(t)}$ and a function of the value of conductivity or sodium concentration Cd$_{(t-\Delta t)}$, Na$_{(t-\Delta t)}$ relating to the preceding control instant.

In a 75th aspect in accordance with the 73rd or 74th aspect, the control flow value to be imposed on the weight loss WLR$_{(t)}$ is calculated a function of the error parameter ERR_BV_UF$_{(t)}$ and a function of the ultrafiltration flow rate value UFR$_{(t-\Delta t)}$ relating to the preceding control instant.

In a 76$^{th}$ aspect in accordance with any one of the preceding aspects from the 30$^{th}$ to the 75$^{th}$, the control unit is configured for:

comparing the measured values of the first parameter BV %$_{mes(t)}$ with a reference threshold, verifying whether the measured value of the first parameter falls below the threshold, and commanding the infusion of a bolus of a predetermined volume of replacement liquid across the infusion line if the verification gives a positive result.

In a 77$^{th}$ aspect in accordance with the preceding aspect, commanding the infusion of the bolus comprises imposing a predetermined flow rate on the infusion pump for a predetermined administration time.

In a 78$^{th}$ aspect in accordance with the 76$^{th}$ and the 77$^{th}$ aspect, the control unit is configured such as to impose, during the administration of the bolus, an ultrafiltration flow rate of zero.

In a 79$^{th}$ aspect, in accordance with the 77$^{th}$ or 78$^{th}$ aspect, commanding the bolus comprises commanding, during administration of the bolus, the second regulating device of the liquid composition such as to impose a predetermined value on the conductivity or sodium concentration Cd$_{(t)}$, Na$_{(t)}$ in the liquid crossing the infusion line.

In an 80$^{th}$ aspect, in accordance with any one of the preceding aspects, the sensor means comprise at least one first sensor S7 active on the extracorporeal circuit for detecting the variation BV % of the blood volume of the patient.

In an 81$^{st}$ aspect, in accordance with any one of the preceding aspects, the sensor means comprise at least one second sensor S6 active on the evacuation line for determining the ultrafiltration flow rate UFR across the membrane, or the weight loss rate WLR of the patient, or a accumulated weight loss WL.

In an 82$^{nd}$ aspect, in accordance with any one of the preceding aspects, the sensor means comprise at least one third sensor S8 active on the dialysis line or on the infusion line or on a common supply line of the dialysis line and the infusion line, the third sensor being a conductivity or concentration sensor predisposed for determining the conductivity of a liquid crossing the dialysis line and/or the infusion line or the sodium concentration of the liquid crossing the dialysis line and/or the infusion line.

In an 83$^{rd}$ aspect, in accordance with any one of the preceding aspects, the sensor means comprise at least one fourth sensor S5 for determining an infusion flow rate Q$_{INF}$ of the replacement fluid crossing the infusion line.

In an 84$^{th}$ aspect, in accordance with any one of the preceding aspects, the sensor means comprise at least one fifth pressure sensor S1, S2, S3, S4 for determining a transmembrane pressure TMP between the first and the second chamber.

An 85$^{th}$ aspect comprises a control unit configured or programmed to perform the control procedure and/or the setting sequence of one of the preceding aspects. The control unit can be of an analog or digital type (for example a CPU with one or more processors) or a combination of analog and digital units.

An 86$^{th}$ aspect comprises a data support for storing instructions which, when performed by a control unit of an apparatus for blood treatment, determine the carrying-out on the apparatus of a control procedure and/or a setting sequence according to any one of the preceding aspects. For example, the data support can comprise a mass memory, for example optical or magnetic, an electromagnetic signal, a re-programmable memory (EPROM, FLASH) or a memory of another nature.

An 87$^{th}$ aspect according to the preceding aspect provides that the setting sequence and the control procedure be contemporaneously performed on the blood treatment apparatus, the setting sequence and control procedure comprising the respective steps described in any one of aspects from the 30$^{th}$ to the 80$^{th}$.

An 88$^{th}$ aspect comprises a method performed using an apparatus for blood treatment of the type of the 1$^{st}$ or of the 2$^{nd}$ aspect, the method comprising executing a control procedure and/or a setting sequence according to any one of the preceding aspects.

An 89$^{th}$ aspect according to the preceding aspect the setting sequence and the control procedure are contemporaneously performed on the blood treatment apparatus, the setting sequence and control procedure comprising the respective steps described in any one of aspects from the 30$^{th}$ to the 80$^{th}$.

In a 90$^{th}$ aspect, it is provided a method of extracorporeal blood treatment executed using an apparatus which comprises: at least one treatment unit, having at least one first chamber and at least one second chamber, separated from one another by a semipermeable membrane, at least one blood removal line connected to an inlet port of the first chamber and predisposed to remove blood from a patient, at least one blood return line connected with an outlet port of the first chamber and predisposed to return treated blood to the patient (the blood removal line, the blood return line and the first chamber being part of an extracorporeal blood circuit), at least one infusion line of a replacement fluid connected with the extracorporeal circuit or directly connectable with a patient and, optionally, a dialysis line connected in inlet to the second chamber, at least one fluid evacuation line connected to an outlet port of the second chamber, and sensor means. The sensor means are positioned and configured such as to determine:

a first parameter relating to a blood volume BV % of the patient;

at least one second parameter relating to a parameter selected from among a group comprising: an ultrafiltration flow rate UFR through the membrane, a weight loss rate WLR of the patient, and an accumulated weight loss WL;

a third parameter Cd, Na relating to a conductivity of a liquid crossing the dialysis line and/or the infusion line or at a concentration in sodium or another predetermined substance of the liquid crossing the dialysis line and/or the infusion line; and a fourth parameter relating to an infusion flow rate $Q_{INF}$ of the replacement fluid crossing the infusion line.

The method comprises performing a control procedure comprising:

receiving, from the sensor means, measured values of the parameters, and calculating, using the measured values and the prescription values of the variation in blood volume BV %$_{target}$, the target weight loss WL$_{target}$, of the plasma conductivity or sodium concentration C$_{target}$, Na$_{target}$, and the infusion volume V$_{INFtarget}$ to be reached in the patient in a predetermined treatment time, the following control values to be set during a time interval after the instant in which the control is made: a conductivity or sodium concentration value Cd$_{(t)}$; Na$_{(t)}$ of the liquid crossing the dialysis line and/or the infusion line; a weight loss rate value WLR$_{(t)}$, and an infusion rate value $Q_{INF(t)}$.

The control procedure may include the respective steps disclosed in any one of aspects from 2$^{nd}$ to 29$^{th}$.

In a 91$^{st}$ aspect, it is provided a method of extracorporeal blood treatment executed using an apparatus which comprises:

at least one treatment unit having at least one first chamber and at least one second chamber, separated from one another by a semipermeable membrane, at least one blood removal line connected to an inlet port of the first chamber and predisposed to remove blood from a patient, at least one blood return line connected to an outlet port of the first chamber and predisposed to return treated blood to the patient (the blood removal line, the blood return line and the first chamber being part of an extracorporeal blood circuit), at least one infusion line of a replacement fluid connected to the extracorporeal circuit or directly connectable with a patient and, optionally, a dialysis line connected in inlet to the second chamber, at least one fluid evacuation line connected with an outlet port of the second chamber, and sensor means. The sensor means are positioned and configured such as to determine:

a first parameter relating to a blood volume BV % of the patient;

at least one second parameter relating to one value selected from among a group comprising: an ultrafiltration rate UFR through the membrane, a weight loss rate WLR of the patient, and an accumulated weight loss WL;

a third parameter Cd, Na relating to a conductivity of a liquid crossing the dialysis line and/or the infusion line or to a sodium concentration or another predetermined substance of the liquid crossing the dialysis line and/or the infusion line; and a fourth parameter relating to a transmembrane pressure TMP between the first and second chamber;

wherein the method comprises performing a control procedure comprising:

receiving measured values of the parameters from the sensor means, and calculating, on the basis of the measured values and the prescription values of the variation of blood volume BV %$_{target}$, the weight loss WL$_{target}$, the plasma conductivity or sodium concentration C$_{target}$, Na$_{target}$ to be reached in the patient in a predetermined treatment time as well as the transmembrane pressure value TMP$_{target}$ to be followed during a predetermined treatment time, the following control values to set during a time interval that is subsequent to the instant of control: a conductivity or sodium concentration value Cd$_{(t)}$, Na$_{(t)}$ of the liquid crossing the dialysis line and/or the infusion line, a weight loss rate WLR$_{(t)}$, and a transmembrane pressure value TMP$_{(t)}$.

The control procedure may include the respective steps disclosed in any one of aspects from 2$^{nd}$ to 29$^{th}$.

A 92$^{nd}$ aspect concerns a method of extracorporeal blood treatment using an apparatus comprising at least one treatment unit having at least one first chamber and at least one second chamber separated from one another by a semipermeable membrane; at least one blood removal line connected to an inlet port of the first chamber and predisposed for removing blood from a patient; at least one blood return line connected with an outlet port of the first chamber and predisposed to return treated blood to the patient. The blood removal line, the blood return line and the first chamber are part of an extracorporeal blood circuit of the apparatus. The apparatus also exhibits:

at least one infusion line of a replacement fluid connected with the extracorporeal circuit or directly connectable to a patient;

at least one dialysis line connected in inlet to the second chamber; at least one fluid evacuation line connected with an outlet port of the second chamber; and sensor means for determining:

a first parameter relating to a blood volume BV % of the patient;

at least a second and a third parameter selected from among: an ultrafiltration flow rate UFR across the membrane, a weight loss rate WLR of the patient (note that the weight loss rate can be derived from the accumulated weight loss WL divided by a time interval), an infusion rate $Q_{INF}$ of the replacement fluid crossing the infusion line;

a fourth parameter relating to a transmembrane pressure TMP between the first and the second chamber.

Further, the apparatus comprises a first regulating device active on at least one of the extracorporeal circuit and the fluid evacuation line and configured such as to regulate an ultrafiltration flow rate UFR or a transmembrane pressure TMP between the first and the second chamber of the treatment unit, wherein the method comprises performing a control procedure in order to regulate the weight loss rate and at least one setting sequence for maximising the convective exchange across the semipermeable membrane.

The control procedure and the setting sequence may include the respective steps disclosed in any one of aspects from $31^{st}$ to $84^{th}$.

DESCRIPTION OF THE DRAWINGS

The invention will be described with the aid of the figures of the drawings, by way of non-limiting example, which illustrate some aspects of the invention.

In particular.

DETAILED DESCRIPTION

There follow descriptions of some examples relating to the structure of the hydraulic part of the apparatus 1: in particular some configurations of the extracorporeal blood circuit are described, of any infusion lines in which a replacement fluid circulates, of the dialysis line, if present, in which a dialysis fluid circulates, and the discharge line of the discharge fluid.

Figure 1:
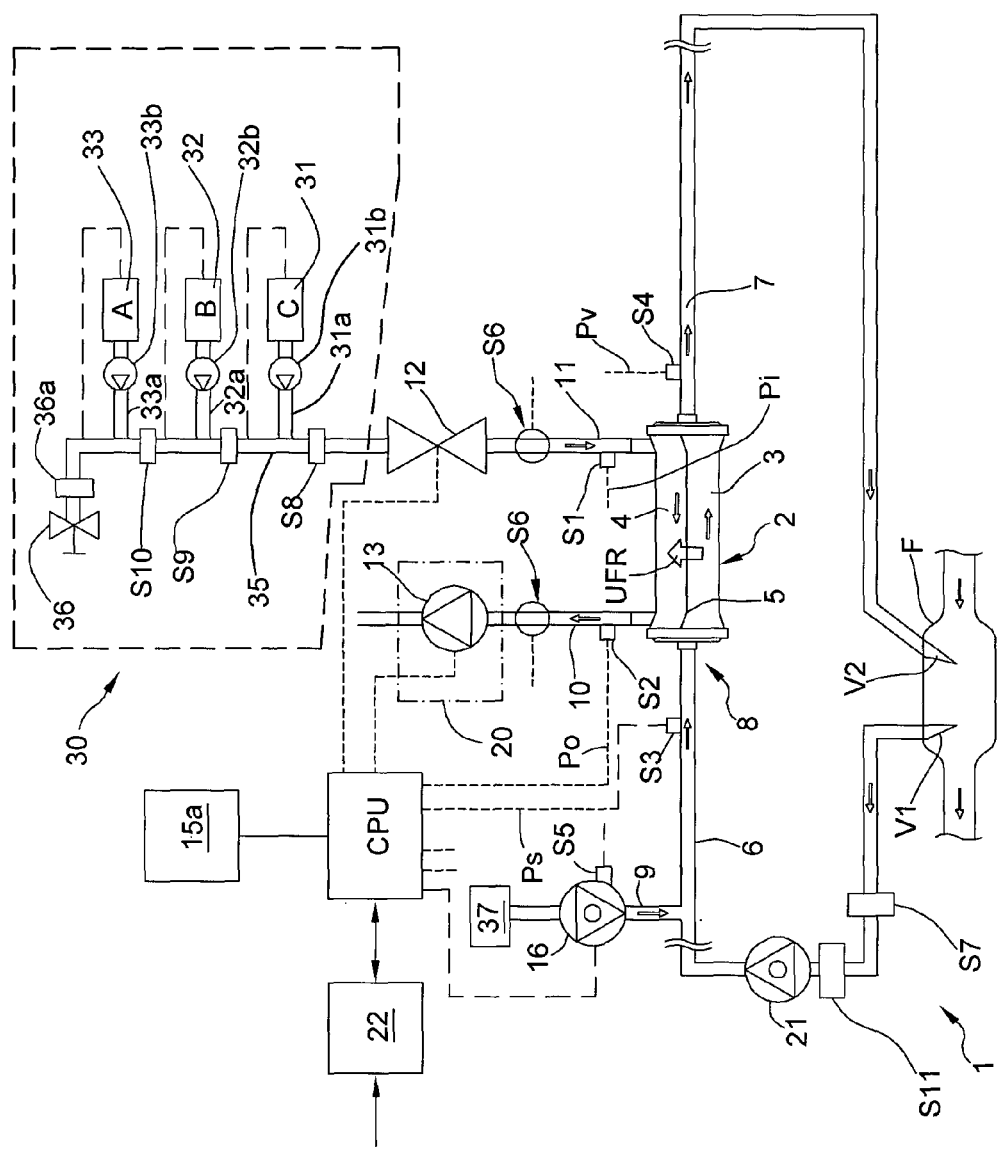
FIG. 1 is a schematic illustration of a first example of a blood treatment apparatus of the invention.
Figure 2:
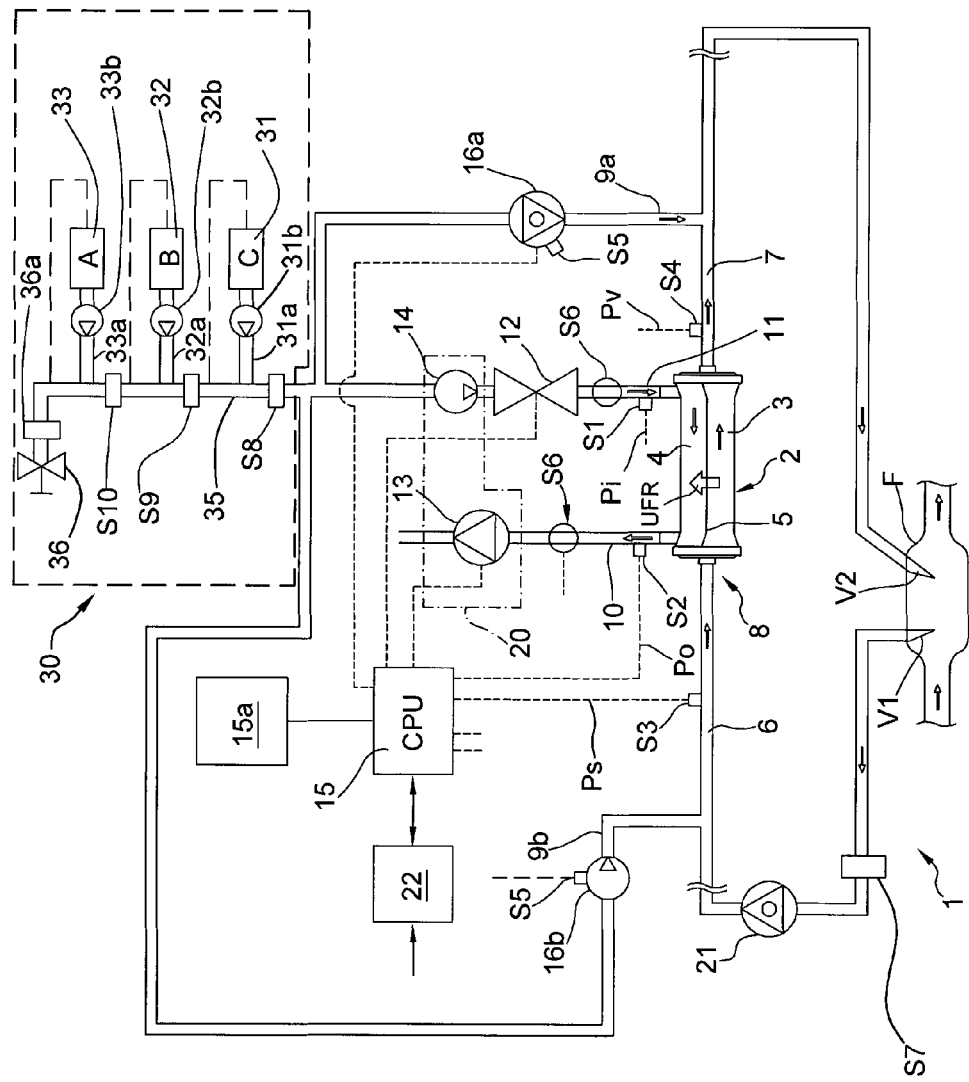
FIG. 2 is a schematic view of a second example of a blood treatment apparatus of the invention.

With reference to FIGS. 1 and 2, 1 denotes in its entirety an apparatus for extracorporeal blood treatment. The apparatus 1 comprises at least one treatment unit 2, for example a hemofilter, a hemodiafilter, a plasma filter, having at least one first chamber 3 and at least one second chamber 4 separated from one another by a semipermeable membrane 5.

A blood removal line 6 is connected with an inlet port of the first chamber 3 and is predisposed, in operating conditions of connection to a patient, to remove blood from a vascular access V1 inserted for example in a fistula F of the patient.

A blood return line 7 connected to an outlet port of the first chamber is predisposed to receive the treated blood from the treatment unit and to return the treated blood to a further vascular access V2 connected with the patient's fistula. Note that the configuration of the vascular access can be of any nature: for example a catheter, a port implanted in the patient, a cannula, a needle, etc. The blood removal line 6, the first chamber 3 of the treatment unit and the blood return line 7 to the patient in practice are part of an extracorporeal blood circuit 8 which, during the use of the apparatus 1, provides for the circulation of the blood externally of the patient's body when subjected to treatment.

In the example of FIG. 1, an infusion line 9 of a replacement fluid is connected to the blood removal line 6, upstream of the first chamber 3. Alternatively, the infusion line 9 might be connected to the return line 7, downstream of the first chamber 3.

In the example of FIG. 2 an infusion line 9a is connected downstream while an infusion line 9b is connected upstream of the unit 2.

With reference both to the example of FIG. 1 and FIG. 2, note that further infusion lines can also be provided, for example connected downstream and/or upstream of the treatment unit.

The apparatus 1 further comprises at least one fluid evacuation line 10 connected with an outlet port of the second chamber 4 for receiving at least a fluid filtered across the semipermeable membrane.

In the examples of FIGS. 1 and 2 there is also a dialysis line 11 for supplying a fresh treatment fluid in inlet to the second chamber 4: the presence of this line is not strictly necessary, as in the absence of the line 11 the apparatus is in any case able to perform treatments such as hemofiltration or plasma filtration. In a case in which the dialysis line 11 is present, a fluid check organ 12 can be used to selectively enable or inhibit a passage of fluid across the dialysis line 11, according to whether it is desired, or not, to have a purification by diffusive effect internally of the treatment unit.

The apparatus 1 comprises sensor means (S1, S2, S3, S4, S5, S6, S7, S8, S9, S10) for determining the values assumed during treatment by the parameters described herein below. There follows a description of sensor means for each of the main parameters to be read. The described sensor means can be present both in the apparatus of FIG. 1 and in the apparatus of FIG. 2.

Transmembrane Pressure (TMP)

During treatment it is necessary to move fluid and undesired particles from the first chamber 3 towards the second chamber 4 of the treatment unit 2. The fluid and/or particle movement creates a transmembrane pressure which is defined as the mean pressure applied on the side of the first chamber towards the side of the second chamber. The transmembrane pressure (hereinafter denoted in abbreviated form as TMP) can be practically determined in various modes. For example the transmembrane pressure TMP can be calculated as follows.

1) In a case in which (see FIGS. 1 and 2) four pressure sensors are present, of which one S1 is on the supply line 11, another S2 on the evacuation line 10, another S3 on the blood removal line 6 and a fourth S4 on the return line 7, the TMP value is determined by the control unit 15 using the pressure signals coming from sensors from S1 to S4, using the formula:

$$TMP = \frac{Ps + Pv}{2} - \frac{Pi + Po}{2}$$

where:
Pi is the pressure detected by sensor S1
Po is the pressure detected by sensor S2
Ps is the pressure detected by sensor S3
Pv is the pressure detected by sensor S4

2) In a case where there are three pressure sensors present, of which one S2 is on the evacuation line 10, another S1 on the supply line 11 and another S4 of the return line 7, the TMP value is determined by the control unit 15, using the pressure signals coming from sensors from said sensors, using the formula:

$$TMP = Pv - \frac{Pi + Po}{2}$$

where:
Po is the pressure detected by sensor S2
Pi is the pressure detected by sensor S1
Pv is the pressure detected by sensor S4

3) Finally, in a case in which two pressure sensors are present, of which one is on the evacuation line 10 and one on the return line 7, the TMP value is determined by the control unit 15 using the pressure signals coming from the sensors S2 and S4, using the formula:

$$TMP = Pv - Po$$

where:
Po is the pressure detected by sensor S2
Pv is the pressure detected by sensor S4

Infusion Flow Rate ($Q_{INF}$)

The apparatus can comprise a sensor S5 of infusion flow rate $Q_{INF}$ of the replacement fluid crossing the infusion line 9 or the infusion lines 9a, 9b. The sensor or sensors S5 for detecting the flow can in practice be volumetric sensors, mass sensors such as for example Coriolis sensors, weight sensors such as for example scales, pump revolution sensors or sensors of still other types: as the type of sensors usable is not significant and since the techniques and the sensors for detecting absolute or differential flow values are known and within the experience of the expert person in the field, no further details thereof are included in the present text.

In the case illustrated in FIGS. 1 and 2, the infusion flow rate sensors comprise sensors S5 destined to determine the number of revolutions of the infusion pumps, by sending a corresponding signal to the control unit 15 which is configured such as to calculate a flow rate along the respective infusion line.

Ultrafiltration Flow Rate (UFR)

The apparatus 1 can further comprise at least one sensor S6 for detecting the ultrafiltration flow rate across the semipermeable membrane 5. For example, a flow sensor S6 can be comprised on the evacuation line 10 and a flow sensor S6 on the dialysis line such as to provide the control unit 15 with the instant value of the respective flows and thus enable the control unit to calculate an instant ultrafiltration flow. Alternatively a differential sensor can be provided, active on the evacuation line and dialysis line and therefore able directly to provide a signal relating to the ultrafiltration flow rate.

The sensor or sensors S6 can in practice be volumetric sensors, mass sensors such as for example Coriolis sensors, weight sensors such as for example scales, pump revolution sensors, or sensors of yet another type: as the type of sensors usable is not significant and since the techniques and the sensors for detecting absolute or differential flow values are known and within the experience of the expert person in the field, no further details thereof are included in the present text.

Weight Loss Rate (WLR)

The weight loss rate WLR can be measured by subtracting the infusion rate (for example as measured above) from the ultrafiltration flow rate (for example as described above) as $UFR = Q_{INF} + WLR$. In other words, having sensors S6 and S5 available, the control unit 15 can be programmed to derive the weight loss rate WLR.

As a further alternative, a sensor can be provided which is able directly to provide a signal which gives the weight loss rate: for example a sensor able to differentially measure the rate taken from the evacuation line and to subtract the flow rate crossing the dialysis line and/or the rate or rates of infusion. The sensor can materially be a mass flow sensor (for example a Coriolis sensor), volumetric, electromagnetic, ponderal (such as a scales able to weigh bags of fluid) or another type.

Blood Volume

The apparatus 1 comprises a sensor S7 for variation of blood volume (BV %) or a parameter from which the variation in blood volume can be calculated in relation to the blood of a patient subjected to treatment. The blood volume variation sensor can for example be optical, able to detect a variation in the optical properties of the blood crossing a calibrated portion of tube.

For example, a blood volume variation sensor can materially comprise calculating, by a control unit, a percentage variation of the blood volume circulating in the patient (BV %) from start of hemodialysis treatment (or hemofiltration, or hemodiafiltration) based on the measurement of the concentration of hemoglobin in the blood, according to the known formula:

$$BV\% = (HGB_0/HGB_t) - 1,$$

where $HGB_0$ represents the concentration of hemoglobin at start of treatment and $HGB_t$ the concentration of hemoglobin at time t in which BV % is calculated.

The hemoglobin concentration is calculated based on the variation of optic absorbance, at a predetermined wavelength, of the blood flowing in the blood removal line 6, across a tract of tube having the appropriate optical properties, precedingly characterised.

Weight Loss

The apparatus 1 can also determine the weight loss over a time period, for example from start of treatment up to a certain instant t: for example the control unit 15 can be programmed to integrate the weight loss rate WLR over the time.

Alternatively, a weight loss sensor can be provided, for example a sensor destined to detect the variation in overall weight of a patient during treatment, or a sensor destined to directly detect the overall weight of the net fluid extracted from a patient.

Conductivity or Sodium Concentration

The apparatus 1 further comprises at least one sensor S8 of conductivity or sodium concentration (or another substance that is to be monitored) of the liquid crossing the dialysis line and/or the infusion line. For example, the conductivity or concentration sensor S8 can be located immediately downstream of a device for regulating a composition of dialysis liquid and/or replacement liquid, which will be more fully described in the following.

First Regulating Device

The apparatus 1 further comprises a first regulating device 20 for regulating ultrafiltration or transmembrane pressure TMP between the first and the second chamber of the treatment unit. The first regulating device 20 is connected to the control unit 15 and active on at least one of the extracorporeal circuit 8 and the fluid evacuation line 10. According to needs and the configuration of the apparatus 1, the first regulating device can comprise for example: a pump 13 located on the fluid evacuation line 10, or two pumps piloted differentially such as two blood pumps located one upstream and one downstream of the filter unit, or a plurality of pumps located on the lines and piloted such as to create an ultrafiltration flow across the membrane, or combinations of one or more pumps and valves appropriately arranged on the blood line or fluid evacuation line, or others besides.

In the example illustrated in FIGS. 1 and 2, the device 20 comprises an ultrafiltration pump 13 operating on the evacuation line and able to recall fluid from the second chamber. In the example of FIG. 2, a treatment fluid supply pump 14 is comprised: in this case the regulating device 20 therefore comprises both the ultrafiltration pump and the supply pump, which are appropriately piloted differentially such as to create an ultrafiltration flow UFR across the membrane. The control unit 15, for example of analog type or a microprocessor, connected with the regulating device, is configured such as to pilot the above-described pumps.

For example, the control unit can operate such as to pilot the device 20 (in the example of FIGS. 1 and 2, the pump or pumps 13 and 14) such that the TMP measured value corresponds to the set value for the TMP. In this case, the control unit acts continuously or periodically on the first regulating device 20 such that, instant by instant, the TMP measured corresponds to the value set at that instant (TMP pressure control). In this way, the ultrafiltration flow rate UFR across the membrane and thus the quantity of fluid removed from the blood present in the first chamber is a function of the TMP imposed. Alternatively, the control unit 15 can be programmed such that the ultrafiltration flow rate UFR follows one or more set values for ultrafiltration flow rate (volumetric control): in this case, the TMP will be variable and the control unit will act such as to maintain the ultrafiltration flow rate constantly close to or equal to the reference value or values predicted or calculated for the UFR. In the following in the present description, some control examples will be described in accordance with aspects of the invention.

The Second Regulating Device.

The apparatus 1 further comprises a second regulating device 30 for regulating a composition of the dialysis liquid and/or the replacement liquid.

In the example of FIG. 1 and FIG. 2, the device 30 comprises one, two or more containers of concentrate 31, 32, 33 located on respective injection lines 31a, 32a, 33a which are predisposed to supply substances such as electrolytes, buffer agents or others towards a preparation line 35 of the liquid located upstream of the dialysis line 11. The concentrate containers can comprise concentrates in the liquid state or solid state, for example powder.

Injection pumps 31b, 32b, 33b can be present on the injection lines to move the fluid along the respective injection line towards the preparation line 35 which collects the liquid, for example water, from a source 36. The source 36 can comprise a water tap or a source of ultra-pure liquid or another besides: the water collected from the source and possibly subjected to filtering stages 36a (not detailed as known and not relevant to the present invention) is provided with the necessary substances by the device 30.

The concentration or conductivity sensor S8, possibly added-to by further concentration or conductivity sensors S9 and S10 located on the line 35, is able to provide the control unit 15 with a relative signal to conductivity or concentration of a predetermined substance (for example sodium) of the fluid crossing the line 35 such that the control unit can act on the second regulating device 30 and in particular on the pumps 31b, 32b, 33b in order to regulate the conductivity Cd or concentration, for example of sodium [Na], of the liquid crossing the dialysis line. In the example of FIG. 1, the infusion line 9 collects the fluid from a source 37 (for example a bag containing replacement fluid) independent with respect to the source 36, while the preparation line 35 exclusively supplies the supply line 11 of the dialysis liquid.

In the example of FIG. 2, differently, both the infusion lines 9a and 9b, as well as the dialysis liquid supply line collect fluid from the supply line 35, such that the conductivity or the concentration of the dialysis fluid crossing the line 11 and the fluid crossing the infusion line 9a, 9b is the same.

Control of the Apparatus

The control unit 15 can comprise one or more digital units, for example microprocessors, or one or more analog units, or a special combination of digital and analog units.

As illustrated in the examples of FIGS. 1 and 2, the control unit is connected with the first and the second regulating devices 20, 30, with a user interface 22, with the sensor means and with the various actuator organs (blood pump 21, infusion pump 16, 16a, 16b, ultrafiltration pump 13, valve 12) located along the lines 7, 8, 9, 9a, 9b, 10, 11 and is configured or programmed to perform the procedures described herein. In a case in which the control unit is programmable, the unit is connected with a data support 15a for storing instructions which, when performed by the control unit, determine performing of the procedures which will be described herein below. The data support can comprise a mass data memory, for example optical or magnetic, a re-programmable memory (EPROM, FLASH) or a memory of another nature.

Figure 3:
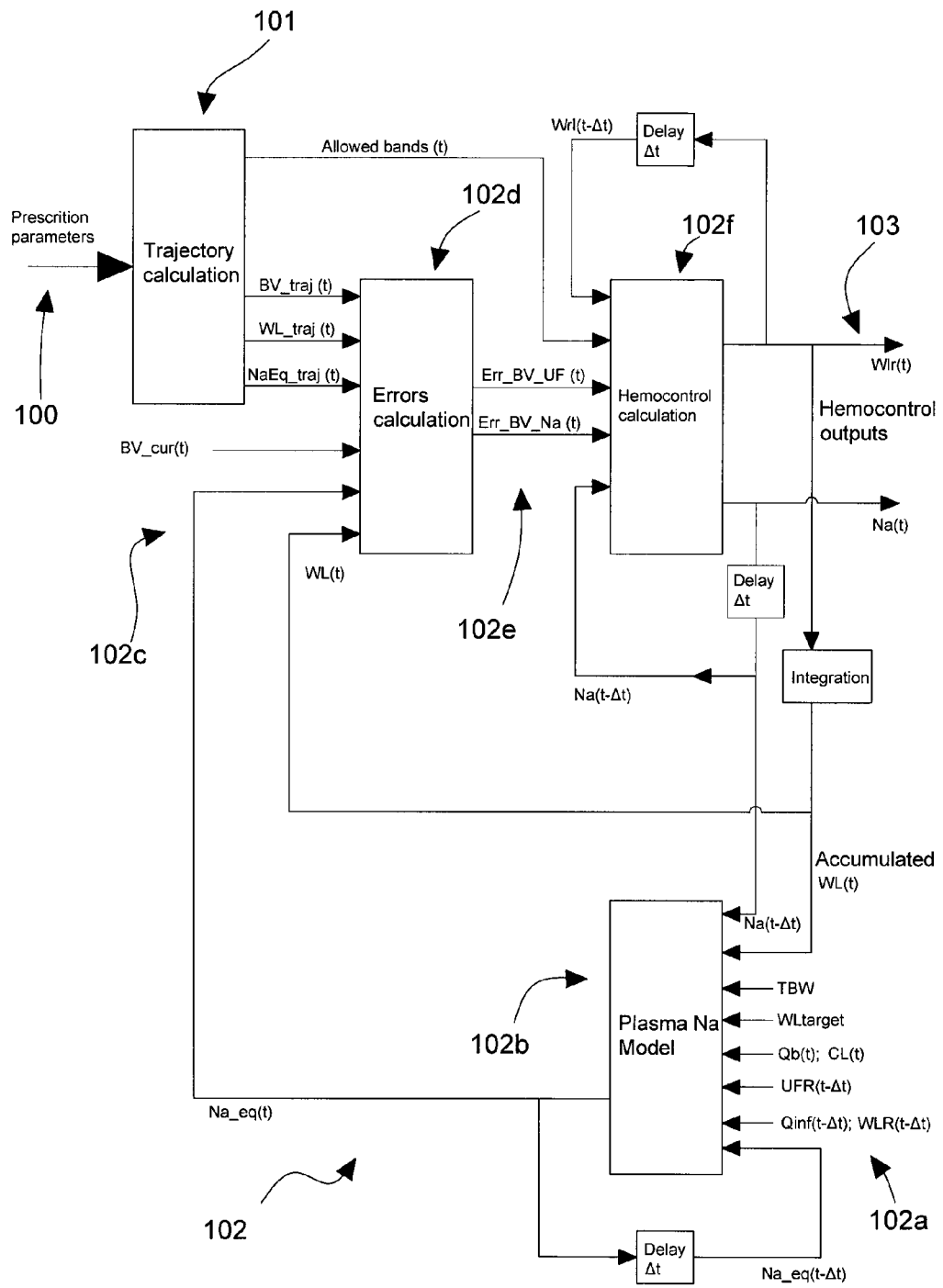
FIG. 3 is a block diagram relating to the periodic calculation by means of a mathematical model M of flow rate control values relating to weight loss and concentration/conductivity imposed on the apparatus.
Figure 4:
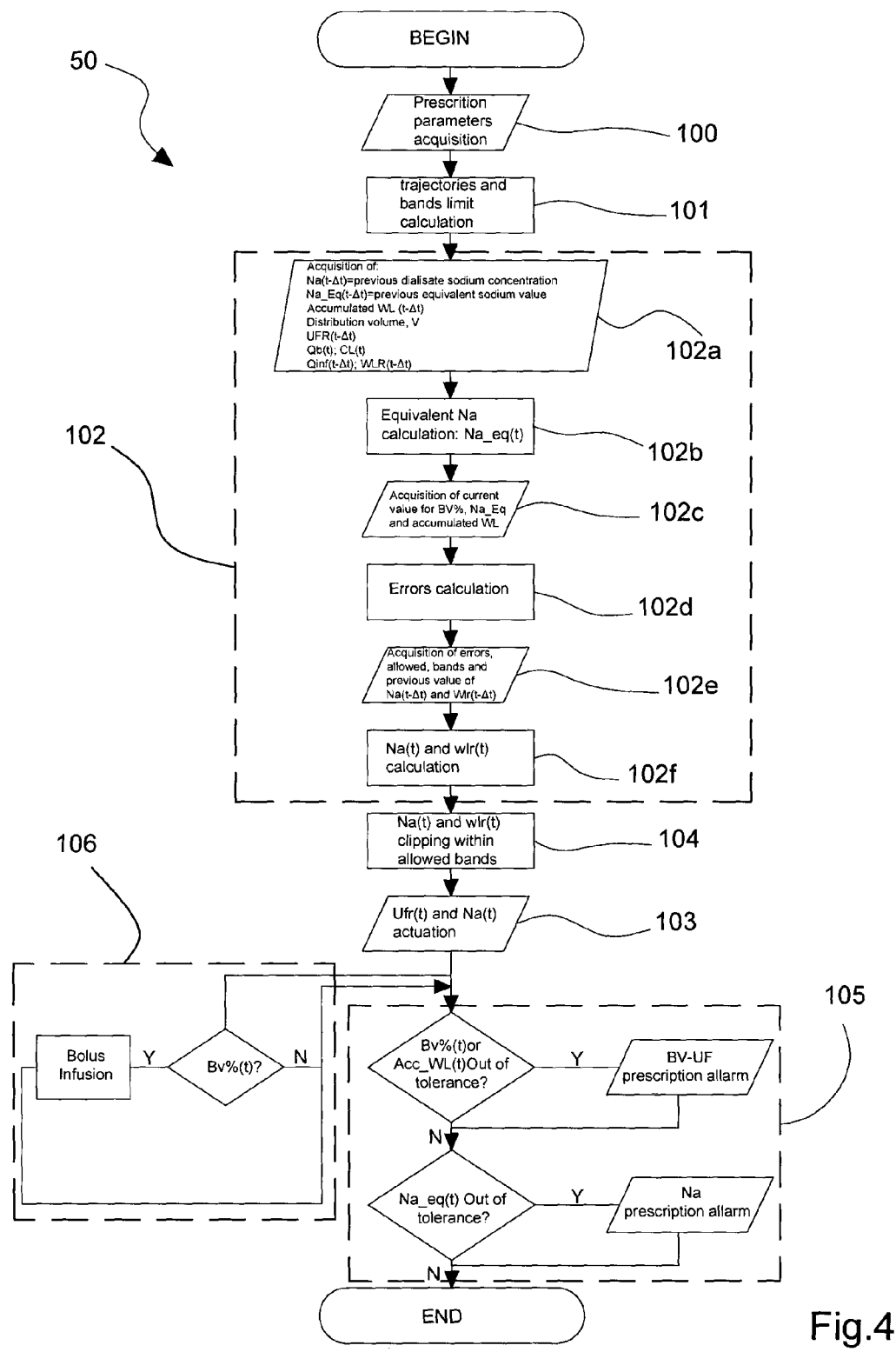
FIG. 4 is a flow diagram showing a control procedure according to an aspect of the invention, which can be carried out by the control unit of an apparatus, for example, of the type illustrated in FIG. 1 or FIG. 2.

In an aspect of the invention (see FIGS. 3 and 4), the control unit 15 is programmed or configured such as to perform, on control instants t temporally one after another (for example the instants t can be temporally equidistant), a control procedure 50 comprising the steps described herein below. As will emerge in more detail, the control unit can be programmed to perform, in agreement with the control procedure, also a TMP setting sequence: the setting sequence of the TMP and the control procedure are coordinated by the control unit such as to prevent negative interactions.

In a first step (step 100), the control procedure comprises receiving, for example via the interface 22, prescription values of the blood volume variation BV $\%_{target}$, of the weight loss $WL_{target}$, the plasma conductivity or sodium concentration $C_{target}$, $Na_{target}$, the volume of infusion $V_{INFtarget}$ to be achieved in the patient in a predetermined treatment time T. For example the user interface can enable entering of the prescription values and the selection of a treatment time in which the prescription values have to be achieved. Alternatively, should it not be intended to impose a predetermined infusion volume as a target to be reached, but rather it is desired to maximise the infusion volume and thus the convective exchange over a predetermined time, the control unit can be programmed to receive prescription values of the blood volume variation BV %$_{target}$, the weight loss WL$_{target}$, the plasma conductivity or sodium concentration C$_{target}$, Na$_{target}$, to be reached in the patient in a predetermined treatment time, as well as a transmembrane pressure value TMP$_{target}$ to be pursued during the treatment with the aim of maximising the convective exchange; this last value is in reality calculated by the setting sequence described herein below.

Thereafter (step 101), the control procedure, having received the prescription values of the blood volume variation BV %$_{target}$, the weight loss WL$_{target}$ to be achieved at end of treatment and having received a treatment time value T, comprises determining, on the basis of the prescription values and the treatment time value T, respective target profiles which describe the desired progression over time of the variation of blood volume BV %$_{target(t)}$, and weight loss WL$_{target(t)}$ (or the weight loss rate WLR$_{target(t)}$. During this stage the target profile which is to describe the conductivity or sodium concentration of the dialysis or infusion liquid. This operation is done in two different ways depending on whether the apparatus 1 is provided or not with a conductivity or concentration sensor directly active on the patient and able to provide the conductivity or sodium concentration. If a plasmatic conductivity sensor S11 is present in the control procedure, for example located on the extracorporeal blood circuit, step 101 is used for determining an target profile which described the desired progression over time of the conductivity or sodium concentration C$_{target(t)}$, Na$_{target(t)}$ that the blood must following during the treatment. Differently, if the apparatus 1 does not comprise a conductivity or concentration sensor directly active on the patient or the extracorporeal blood circuit, during stage 101 the procedure generates an target profile which describes the desired progression over time of the equivalent sodium concentration Nq$_{eq-target(t)}$: in practice the control unit 15 is programmed or configured such that during the treatment the control procedure iteratively determines the equivalent sodium concentration Na$_{eq(t)}$ on the basis of a mathematical model M and compares the equivalent sodium concentration Na$_{eq(t)}$ with the respective target profile.

The control procedure (step 102) comprises receiving, from the sensor means, measured values of blood volume BV %$_{mes}$, of the ultrafiltration flow rate or weight loss rate UFR$_{mes}$, WLR$_{mes}$ (or alternatively accumulated weight loss WL$_{mes}$), of the conductivity or sodium concentration in the liquid crossing the dialysis line and/or the infusion line Cd$_{mes}$; Na$_{mes}$ and the infusion flow rate Q$_{INFmes}$. Alternatively or additionally to the infusion flow rate Q$_{INFmes}$ the control unit can also receive a measured value of the transmembrane pressure TMP$_{mes}$.

The control procedure also comprises calculating, in accordance with the measured values and the prescription values of the blood volume variation BV %$_{target}$, the weight loss WL$_{target}$, the plasma conductivity or sodium concentration C$_{target}$, Na$_{target}$, the infusion volume V$_{INFtarget}$ to be reached in the patient in a predetermined treatment time, the following control values to impose during a time interval after the control instant.

The control values that are determined comprise:
  a conductivity or sodium concentration value Cd$_{(t)}$; Na$_{(t)}$ of the liquid crossing the dialysis line and/or the infusion line;
  a weight loss rate value WLR$_{(t)}$,
  an infusion rate value Q$_{INF(t)}$.

In other words, the control unit is able to receive the measured values and the respective prescription values and to generate values that are then used to regulate the composition of the dialysis and/or infusion values, the weight loss rate and the infusion flow rate, thus realising a system able to guarantee a high degree of comfort for the patient and a predefined convective exchange (that is, the infusion rate under carefully controlled conditions).

Alternatively, the control procedure comprises calculating the following control values to be imposed during a time interval following the control instant based on: the measured values of the blood volume variation BV %$_{mes}$, the ultrafiltration flow rate UFR$_{mes}$ or the weight loss rate WLR$_{mes}$ (or alternatively the accumulated weight loss WL$_{mes}$), the conductivity or sodium concentration of the liquid crossing the dialysis line and/or the infusion line Cd$_{mes}$, Na$_{mes}$ and the transmembrane pressure TMP$_{mes}$, and the prescription values of the blood volume variation BV %$_{target}$, the weight loss WL$_{target}$, the plasma conductivity or sodium concentration C$_{target}$, Na$_{target}$, to be achieved in the patient over a predetermined treatment time and the transmembrane pressure TMP$_{target}$ to be observed during the treatment.

The control values that are determined comprise:
  a conductivity or sodium concentration value Cd$_{(t)}$; Na$_{(t)}$ of the liquid crossing the dialysis line and/or the infusion line;
  a weight loss rate value WLR$_{(t)}$,
  a transmembrane pressure value TMP$_{(t)}$.

In other words, in accordance with a second aspect the control unit is able to receive the above-mentioned measured values and the respective prescription values and to generate values that are then used to regulate the composition of the dialysis liquid and/or the infusion liquid, the weight loss rate and the TMP, thus realising a system able to guarantee a high degree of comfort for the patient and an optimum convective exchange (the TMP being controllable for example in order to maximise the convective exchange).

Once the control values have been determined at instant t, the control values are imposed during a time interval Δt following the control instant t (step 103). In more detail, the control value relating to the conductivity or sodium concentration Cd$_{(t)}$; Na$_{(t)}$ is imposed by the control unit 15 commanding the second regulating device 30, the control values relating to the weight loss rate WLR$_{(t)}$ and the infusion flow rate Q$_{INF(t)}$ are imposed by the control unit by acting on the first regulating device 20 and on the pump 16 or pumps 16a, 16b. If the measured value is the TMP, the control values relating to the weight loss rate WLR$_{(t)}$ and the transmembrane pressure TMP$_{(t)}$ are imposed by the control unit once more by acting appropriately on the first regulating device 20 and the pump 16 or pumps 16a, 16b. Note that in the example of FIG. 2, the control unit commands the second regulating device 30 and thanks to the above-described hydraulic configuration imposes the same conductivity or sodium concentration on both the dialysis liquid and the infusion liquid or liquids.

A previously mentioned, the apparatus 1 can also not exhibit a conductivity or concentration sensor directly acting on the patient or on the extracorporeal blood circuit. In this case, the control procedure uses a mathematical model M representing a kinetics of solutes in a distribution volume V in the patient for iteratively calculating, at each control instant t, an equivalent sodium concentration value Na$_{eq(t)}$. The model M can for example be memorised in the memory 15a associated to the control unit which is configured to acquire (step 102a) and apply the following values in inlet to the mathematical model:

a control value of the equivalent concentration relating to a preceding control instant ($Na_{eq(t-\Delta t)}$), a control value of the conductivity or sodium concentration value of the dialysis liquid at a preceding control instant ($Cd_{(t-\Delta t)}$; $Na_{(t-\Delta t)}$), a control value relating to the ultrafiltration rate at a preceding instant ($UFR_{(t-\Delta t)}$), a control value relating to the weight loss rate at a preceding control instant $WLR_{(t-\Delta t)}$ and/or a control value relating to the infusion rate at a preceding control instant $Q_{INF(t-\Delta t)}$, a accumulated weight loss up to a preceding control instant ($WL_{mes(t-\Delta t)}$), or a accumulated weight loss value up to a control instant ($WL_{mes(t)}$), a total convective and diffusive clearance value measured at control instant $Cl_{mes(t)}$ or an estimated total convective and diffusive clearance value $Cl_{mes(t)}$ (for example in a case of estimated clearance value this value can be calculated according to a current measured value of the infusion flow rate $Q_{INFmes(t)}$ and one of the current measured values of the blood flow $Q_{B(t)}$ and the current diffusive clearance value $Cl_{diff(t)}$; alternatively the estimated clearance value can be mathematically derived from preceding values assimilated from C1);

a reference value relating to the volume V of distribution of the solutes in the patient or the corporeal water volume TBW. The distribution volume V is determined for each patient on the basis of the weight loss objective $WL_{target}$, the total accumulated weight loss $WL_{(t)}$ and the volume of corporeal water TBW; the last value is estimated as described herein below.

Example of Mathematical Model M

Figure 14:
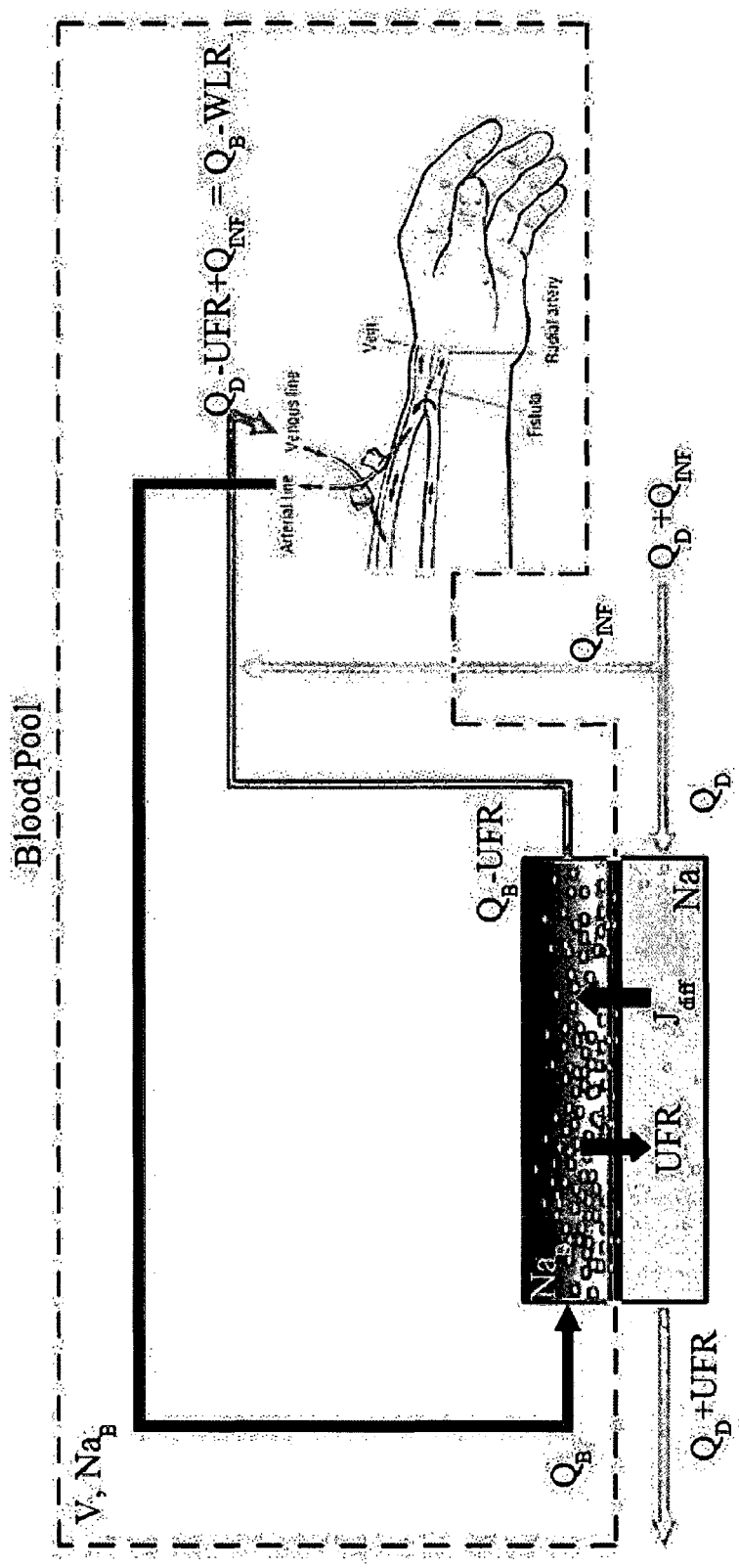
FIG. 14 shows the system constituted by the patient and the treatment unit to which reference is made in determining the mathematical model M in accordance with aspects of the invention.

An example of mathematic model M is now illustrated, with reference to the system constituted by the patient and the treatment unit illustrated in FIG. 14.

The following symbols are used:

$J_{diff}$=Mass flow of sodium across the membrane due to the diffusive process;

$J_{conv}$=Mass flow of sodium across the membrane due to the convective process;

UFR=Total ultrafiltration across the membrane: $Q_{INF}$+WLR;

$Na_B$=Plasma sodium concentration;

$Q_B$=Blood flow;

Na=Sodium concentration in the dialysis liquid;

$Q_D$=Dialysis liquid flow rate;

$Q_{INF}$=Infusion liquid flow rate;

WLR=Weight loss rate;

V=Sodium distribution volume in the patient.

The mass balance equation for the system can be represented as (see the system of FIG. 14):

$$\frac{dM}{dt} = \frac{d}{dt}(V(t) \cdot Na_B(t)) = Q_{INF}(t) \cdot Na(t) + J_{diff} - J_{conv} \quad (1)$$

From the definition of diffusive clearance $Cl_{diff}$, the following obtains:

$J_{diff}=Cl_{diff}(Na(t)-Na_B(t))$ $Cl_{diff}$ can be measured directly or approximately considering: $CL_{diff}=Q_B/2$.

The convective transport is given by:

$J_{conv}=UFR(t) \cdot Na_B(t) \cdot SV$

Where:

SV=Sieving coefficient of the membrane (assumed to be 1 for sodium)

By substituting $J_{diff}$ and $J_{conv}$ the equation (1) becomes:

$$\frac{dM}{dt} = \frac{d}{dt}(V(t) \cdot Na_B(t)) = Na(t) \cdot (Cl_{diff} + Q_{INF}(t)) - Na_B(t) \cdot (Cl_{diff} + UFR(t)) \quad (2)$$

The sodium distribution volume during the treatment can be expressed as:

$V(t)=TBW+WL_{target}-WL(t)$ where:

TBW=estimated volume of corporeal water (see below for some of the estimation methods for TWB);

$WL_{target}$=prescription value of weight loss;

WL(t)=weight loss achieved at time t.

From equation (2) the following equation system can be derived, obtained by considering the various infusion flow rate values applied during the treatment ($Q_{INF1}$, $Q_{INF2}$ ... $Q_{INFn}$):

$$\begin{cases} \frac{dM_1}{dt} = Na(t) \cdot (Cl_{diff} + Q_{INF1}) - \\ \quad Na_B(t) \cdot (Cl_{diff} + UFR(t)) \end{cases} \text{for } 0 < t \leq t_1 \\ \begin{cases} \frac{dM_2}{dt} = Na(t) \cdot (Cl_{diff} + Q_{INF2}) - \\ \quad Na_B(t) \cdot (Cl_{diff} + UFR(t)) \end{cases} \text{for } t_1 < t \leq t_2 \\ \dots \\ \begin{cases} \frac{dM_2}{dt} = Na(t) \cdot (Cl_{diff} + Q_{INF2}) - \\ \quad Na_B(t) \cdot (Cl_{diff} + UFR(t)) \end{cases} \text{for } t_{n-1} < t \leq t_n \quad (3)$$

Each equation can be resolved by integration on the corresponding time interval.

From the definition of sodium equivalent concentration it follows that the plasma sodium concentration at time t, obtained by profiling the sodium concentration in the dialysis liquid $Na_{(t)}$ in the time interval from 0 to t, must be equal to the plasma sodium concentration, obtained by applying a constant sodium concentration value $Na_{eq}$ in the same time interval, and therefore:

$Na_B(t)|_{Na(t)}=Na_B(t)|_{Na_{eq}}$ (4)

Resolving system (3) with respect to the plasma sodium concentration $Na_{B(t)}$, in accordance respectively with $Na_{(t)}$ and $Na_{eq}$, and imposing equality (4), a mathematic relation can be determined which expresses the equivalent concentration of sodium as a function of time $Na_{eq(t)}$. This expression can also be written in recursive form, starting from a knowledge of the assumed equivalent sodium concentration value at the instant of the preceding calculation $Na_{eq(t-\Delta t)}$.

In output from the mathematical model M, the control procedure enables (step 102b) the value of an equivalent sodium concentration $Na_{eq(t)}$ to be obtained at the control instant t which is then related to a respective target value for the equivalent conductivity or sodium concentration $C_{eq-target}$, $Na_{eq-target}$ and used for determining the above-described control values at the control instant (step 102).

The mathematical model M is representative of a kinetics of the solutes in a distribution volume in the patient V according to a single-compartment model. As mentioned herein above, the distribution volume V is determined for each patient on the basis of the weight loss objective $WL_{target}$, the total accumulated weight loss $WL_{(t)}$ and the volume of corporeal water TBW estimated for example on the basis of information such as age, sex, height and weight of the patient. For example, some example formulae for calculating the volume of corporeal water TBW are the following:

Input parameters: Sex, Height [cm], Weight [Kg], Age [years], Volume %

Output parameters: volume of corporeal water (TWB)

if Sex="Male", then $$TWB=2.447-(0.09516*Age)+(0.1074*Height)+(0.3362*Weight)$$

if Sex="Female", then $$TWB=-2.097+(0.1069*Height)+(0.2466*Weight) \quad \text{Watson's Formula}$$

if Sex="Male", then $$TWB=(0.194786*Height)+(0.296785*Weight)-14.012934$$

if Sex="Female", then $$TWB=(0.344547*Height)+(0.183809*Weight)-35.270121 \quad \text{Hume-Weyer's Formula}$$

if Sex="Male" and Height≤132.7 cm, then $$TWB=-1.927+(0.465*Weight)+(0.045*Height)$$

if Sex="Male" and Height>132.7 cm, then $$TWB=-21.993+(0.406*Weight)+(0.209*Height)$$

if Sex="Female" e Height≤110.8 cm, then $$TWB=0.076+(0.507*Weight)+(0.013*Height)$$

if Sex="Female" e Height>110.8 cm, then $$TWB=-10.313+(0.252*Weight)+(0.154*Height) \quad \text{Mellits-Cheek's Formula}$$

$$TWB=Weight*Volume\%/100 \quad \text{Percentage Formula}$$

As has been described, the control procedure imposes a variable concentration or conductivity on the dialysis liquid and/or the infusion liquid; in this situation, the constant concentration of sodium in the dialysis liquid is defined as equivalent sodium concentration at instant t, which constant concentration, if applied from the start of the treatment up to a certain instant t would lead to a same plasma sodium concentration in the patient as that which is obtained at the same instant t with the sodium concentration variation or conductivity imposed by the control procedure up to the time t.

Figure 11:
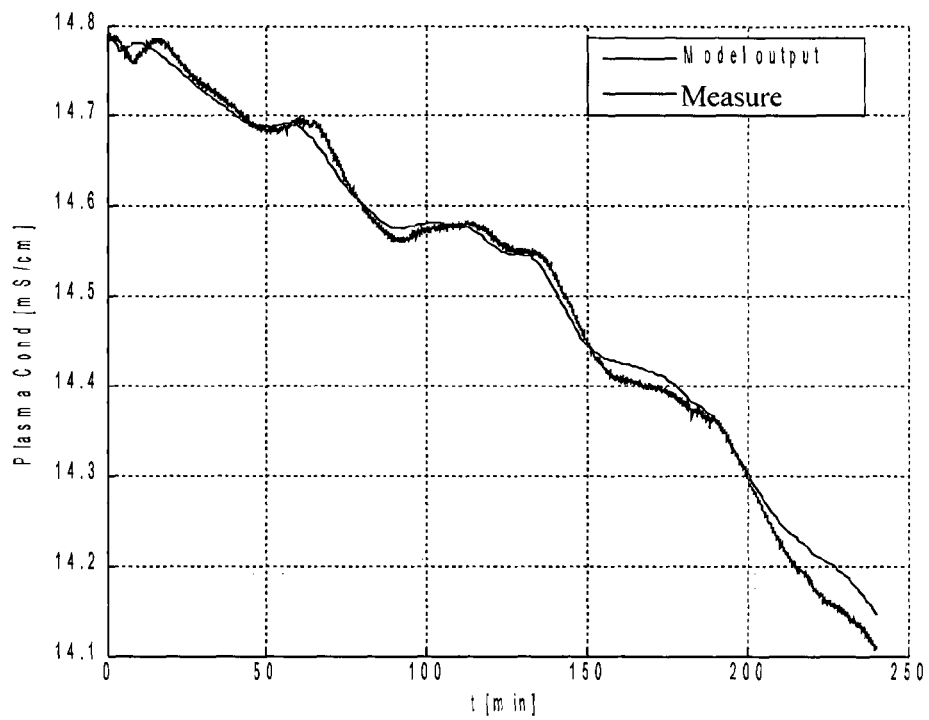
FIGS. 10 and 11 comparatively illustrated the progression of the plasmatic conductivity measure experimentally on a patient and the progression of the estimated plasma conductivity using the mathematical model M in accordance with aspects of the invention.
Figure 10:
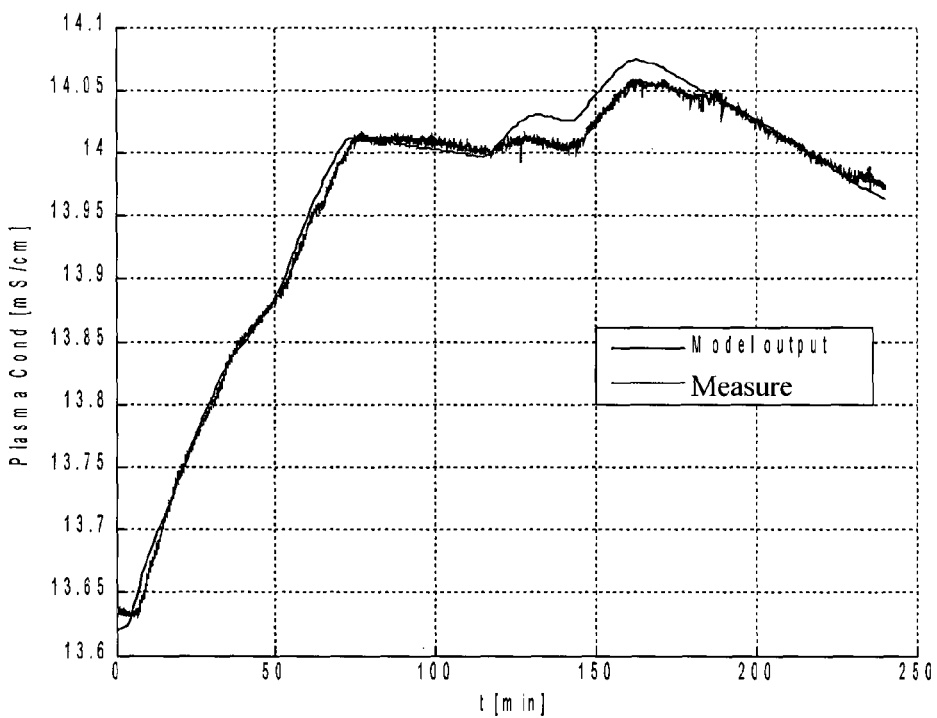
Figure 12:
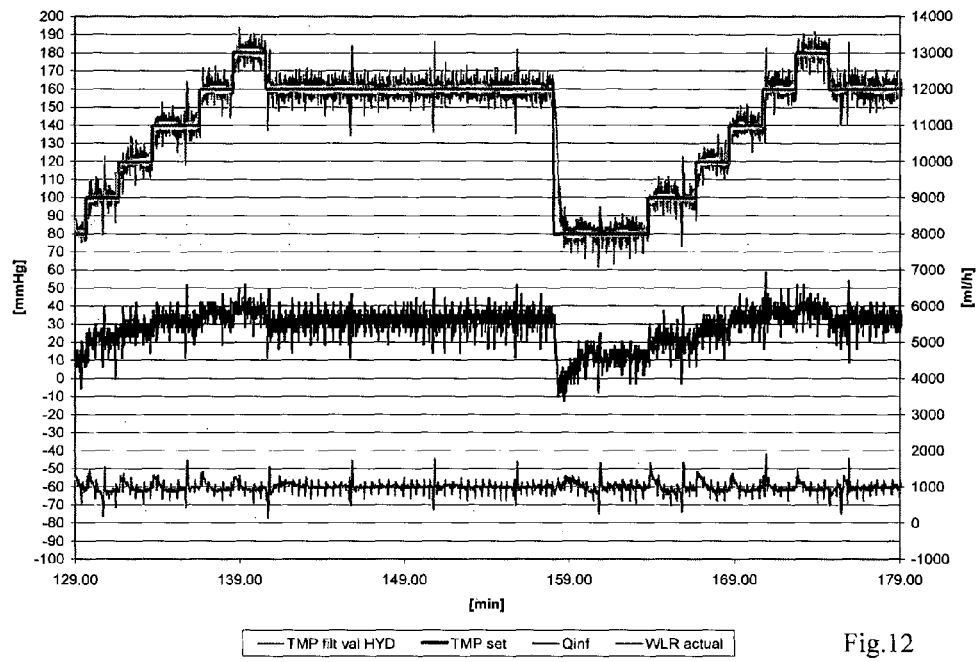
FIGS. 12 and 13 show the progression of the set value of the TMP determined by the setting sequence respectively in the case of constant weight loss rate and in the case of varied weight loss rate during a same setting sequence, for example on the action of the control procedure in accordance with aspects of the invention.
Figure 13:
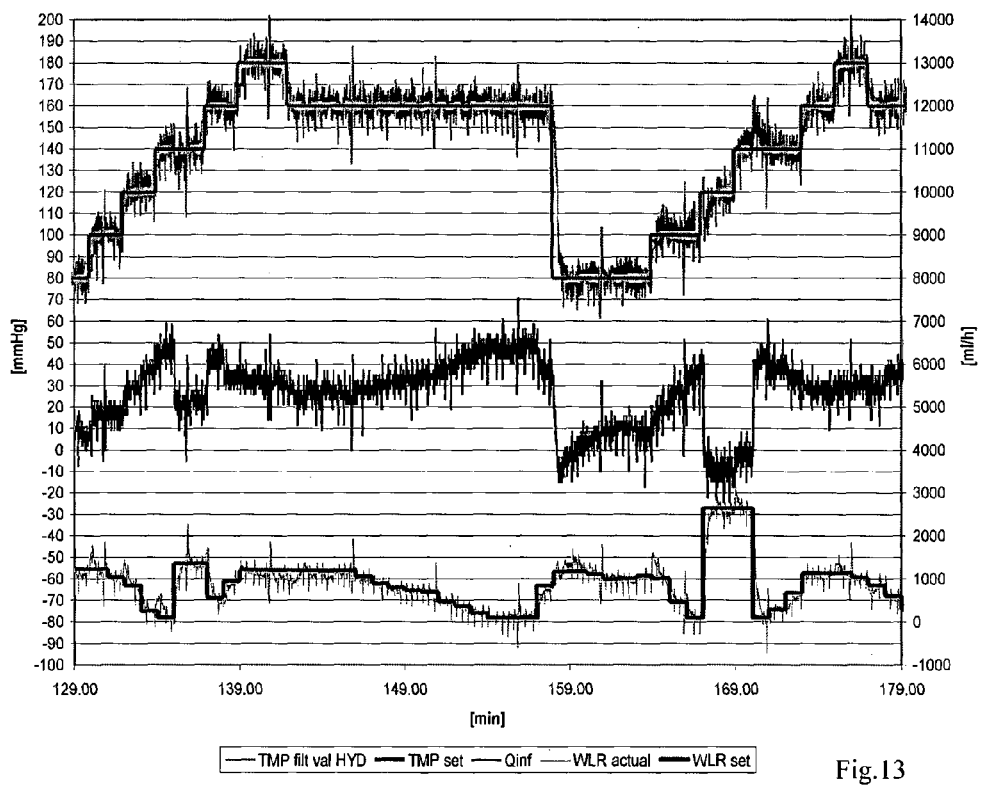

FIGS. 10 and 11 show a clear convergence between the plasma conductivity measured experimentally and the plasma conductivity calculated using the model M: this confirms the accuracy of the mathematical model used.

In practice, once the equivalent sodium concentration value $Na_{eq(t)}$ is obtained at the control instant t (sub-step 102b) and once (sub-step 102c) in possession of the measured values of the variation in blood volume BV $\%_{mes}$ and the weight loss $WL_{mes}$ (or the weight loss rate $WLR_{mes}$), the control procedure comprises a further sub-step of calculating the error (102d) which comprises determining at least one first error parameter $ERR\_BV\_UF_{(t)}$ according to the difference between the measured value of the first parameter BV $\%_{mes}$ at the control instant t and a corresponding value on the target profile relating to the variation in blood volume in the time BV $\%_{target(t)}$ and the difference between a measured value of the weight loss $WL_{mes}$ (or the weight loss rate $WLR_{mes}$) at the control instant t and a corresponding value given by the target profile relating to the weight loss $WL_{target(t)}$ (or respectively the weight loss rate $WLR_{target(t)}$) in the time. The stage of calculating the error also comprises determining at least one second error parameter $ERR\_BV\_Na_{(t)}$ as a function of the difference between the equivalent sodium concentration value $Na_{eq(t)}$ at the control instant t and a corresponding value on the target profile relating to the variation over the time of the equivalent sodium concentration $Na_{eq-target(t)}$, and the difference between the measured value of the first parameter BV $\%_{mes}$ at the control instant t and the corresponding value on the target profile in relation to the variation in blood volume in the time BV $\%_{target(t)}$.

When the first and the second error parameters have been obtained, the control procedure performed by the unit 15 comprises calculating (sub-step 102f) the control value of conductivity or sodium concentration $Cd_{(t)}$, $Na_{(t)}$ to be imposed in the liquid crossing the dialysis line and/or the infusion line according to the second error parameter $ERR\_BV\_Na_{(t)}$ and the conductivity or sodium concentration value $Cd_{(t-\Delta t)}$, $Na_{(t-\Delta t)}$ relating to the preceding control instant and previously acquired (sub-step 102e). Further, the control procedure performed by the unit 15 comprises calculating (sub-step 102f) the control value to be set on the weight loss rate $WLR_{(t)}$ which is calculated according to the first error parameter $ERR\_BV\_UF_{(t)}$ and according to the ultrafiltration flow rate $UFR_{(t-\Delta t)}$ relative to the preceding control instant.

It should be noted that before true and proper actuation of the control values as above-determined, a step of verification can be included in which it is verified that the control values are within predetermined bands; a step of adjusting the control values themselves (step 104), if required, is also included. Further, the control procedure can comprise a stage of verification and alarm 105 comprising verifying whether the measured values of the first parameter BV $\%_{mes(t)}$, the second parameter $UFR_{mes(t)}$, $WLR_{mes(t)}$, $WL_{mes(t)}$, the third parameter $Cd_{mes(t)}$, $Na_{mes(t)}$, and/or the equivalent concentration $Na_{eq(t)}$ exceed or not the respective safety threshold values.

It should also be noted that the control procedure can include a compensation sequence (step 106) which comprises comparing the measured values of the first parameter BV $\%_{mes(t)}$ with a reference threshold and verifying whether the measured value of the first parameter falls below the threshold and commanding infusion of a bolus of predetermined replacement liquid volume into the infusion line if the verification gives a positive outcome. The bolus infusion can be done by imposing a predetermined rate over a predetermined administration time on the infusion pump and appropriately commanding the second regulating device 30, for example in such a way as to increase the sodium concentration in the infusion liquid for a brief time interval. During the infusion of the bolus the control procedure can comprise imposing an ultrafiltration flow rate UFR of zero.

In a further aspect of the invention, the control unit can be programmed also to perform, in addition to the control procedure as described above, a setting sequence 200 (see FIG. 5) of the transmembrane pressure TMP. This type of sequence is performed if it is intended to control the apparatus also on the basis of the TMP and for example to maximise as much as possible the infused fluid volume, thus increasing the convective exchange. The setting sequence is performed at a setting instant indicated by T and possibly repeated a plurality of times during a treatment. For example the setting sequence can be performed while the control procedure is contemporaneously performed. For example, the control unit is configured to repeat both the control procedure (at a plurality of control instants t that are temporally consecutive to one another) and the control procedure of the TMP (at a plurality of control instants t that are temporally consecutive to one another). In practice the control unit is configured to impose the control value or values determined using the control procedure during a time interval Δt following each control instant t, cyclically repeating the control procedure during the whole treatment. In parallel, the control unit is also configured to perform the setting sequence at a plurality of setting instants τ temporally consecutive to one another, imposing the TMP thus determined. In the illustrated embodiment described herein the control unit is configured to perform the control procedure at more frequent control instants with respect to the setting instants in which the setting sequence is performed.

In more detail with regard to the setting sequence, the sequence comprises the following steps, aimed at identifying an optimal value of TMP at which a maximisation of the ultrafiltration is obtained.

The sequence comprises, for example by acting on the pump 13 of the first regulating pump 20, determining a first increase $\delta TMP_n$ (step 201) to reach a second transmembrane pressure value $TMP_{n+1}$; then the sequence comprises measuring or calculating (step 202) a variation $\Delta UFR_{(n)}$ between the ultrafiltration flow UFR across the membrane 5 at the first transmembrane pressure $TMP_n$ and the ultrafiltration flow UFR at the second transmembrane pressure $TMP_{n+1}$: the variation of the ultrafiltration flow is determined either by direct measuring of the ultrafiltration flow or indirectly by taking account of both the flow variations of the replacement liquid $\Delta Q_{INF(n)}$ along the infusion line and the variations of weight loss rate $\Delta WLR_{(n)}$ due to the control procedure. Following this the control sequence comprises comparing (step 203) the ultrafiltration variation $\Delta UFR_{(n)}$ with a reference value and, if the variation value $\Delta UFR_{(n)}$ is greater than the reference value, commanding the first regulating device 20 to impose a second increase $\delta TMP_{n+1}$ on the transmembrane pressure in order to reach a third transmembrane pressure value $TMP_{n+2}$, and so on, cyclically repeating the described sequence for successive increases.

Figure 5:
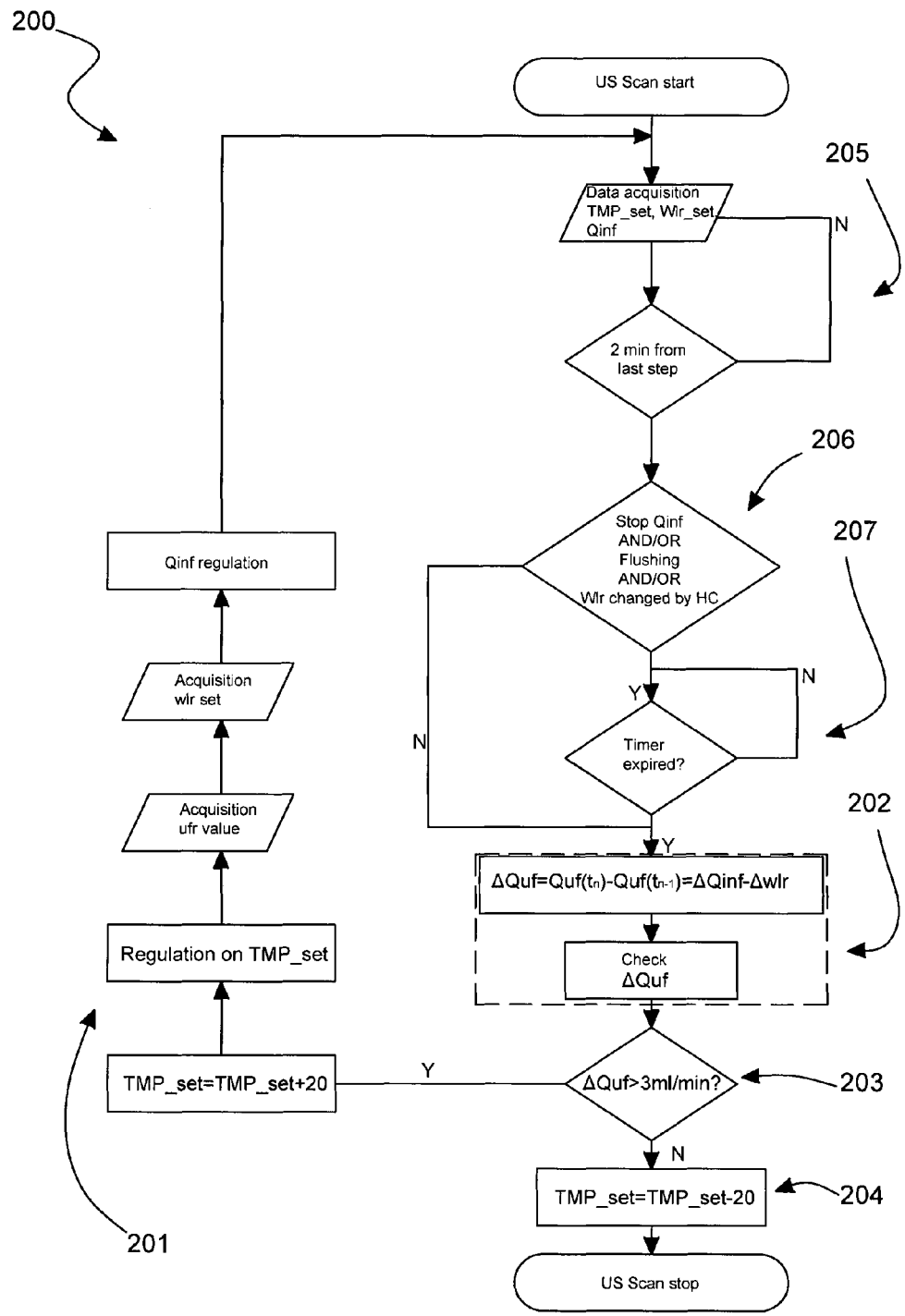
FIG. 5 is a flow chart showing a setting sequence according to an aspect of the invention, which can be carried out by the control unit of an apparatus for example of the type illustrated in FIG. 1 and FIG. 2, during performance of the control procedure of FIG. 4.

In the example of FIG. 5, the ultrafiltration flow rate variation ΔUFR is compared at step 203 with a reference flow rate, for example 3 ml/min and, should the ultrafiltration flow rate be greater than 3 ml/min, the ultrafiltration pump 13 is commanded such as to set an increase of TMP that is greater than the preceding one. In this way, if following the first TMP variation the corresponding variation in ultrafiltration flow rate is sufficiently high and therefore such as to indicate that the treatment unit is operating in a sufficiently distant zone from the plateau zone (with reference to the characteristic Ultrafiltration/TMP curve relating to the treatment unit), the above-described sequence is repeated, newly increasing the TMP (step 201).

Note that, for example, the control unit can considerably increase the amplitude of the following pressure increase, in this way accelerating the search for and the setting of the optimal TMP. If on the other hand the value of the variation ΔUFR of the ultrafiltration flow (step 203) is lower than the reference value, the TMP setting procedure is interrupted, as will be more fully described herein below, as the unit in this case considers that it has reach the optimal TMP and thus maintains it as the set value (step 204).

Figure 6:
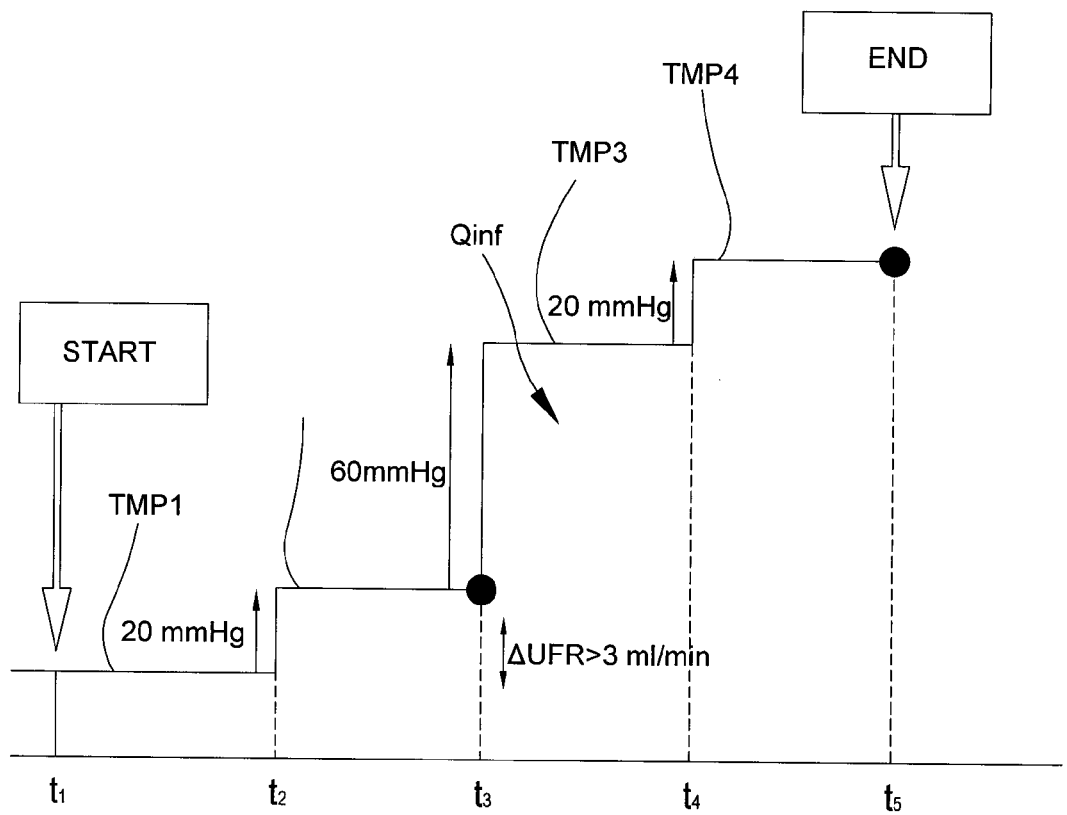
FIG. 6 is a time chart showing the progression of the transmembrane pressure TMP during a setting sequence of the TMP, in an aspect of the invention.

FIG. 6 shows a system of Cartesian axes in which the x-axis represents the time and the y-axis the TMP pressure the pressure TMP set instant by instant: FIG. 6 shows an embodiment of a sequence of TMP setting that can be performed by a control unit which is part of the apparatus 1 of the type illustrated in FIG. 1 or FIG. 2. Following a manual command or an automatic procedure, a TMP setting sequence is started by the control unit. At first (START in FIG. 6), the control unit maintains the TMP at a value of $TMP_1$ for a first time interval $t_1$-$t_2$. At the end of the first time interval $t_1$-$t_2$, a pressure increase of 20 mmHg is imposed on the set TMP value, passing to a set value of $TMP_2$, with a consequent activation of the ultrafiltration pump 13 and the infusion pump 16 (or at least one of the pumps 16a, 16b in the case of FIG. 2). If, in interval $t_2$-$t_3$, the variation in ultrafiltration flow rate ΔUFR is greater than 3 ml/min, for example 12 ml/min, the successive increase in the set value of TMP is optionally imposed at greater than 20 mmHg and, in the illustrated example, at 60 mmHg. Note that in the meantime if the control procedure performed during the setting has varied the weight loss rate WLR the control unit would take account of it in evaluating the effective rise in ultrafiltration at each TMP rise: either the variation ΔUFR is measured directly or, if the variation is calculated on the basis of the variation in the infusion flow, the eventual contribution given by the flow variation of weight loss WLR is added to the infusion flow. In response to the new set value of TMP, i.e. $TMP_3$, the control unit also commands the acceleration of the infusion pump such as to balance the effect of the greater ultrafiltration. Note also that the duration of the interval $t_3$-$t_4$ is not necessary equal to that of the interval $t_2$-$t_3$: for example the unit 15 can be configured to impose a variable interval, which becomes greater as a function with the increment in TMP that precedes it, with the aim of enabling a transitory of adaptation for the ultrafiltration pump and the infusion pump or pumps.

Still with reference to FIG. 6, at instant $t_4$ a new TMP increase is imposed, 20 mmHg, and after a further interval T (in FIG. 6: $t_4$-$t_5$), the increase in the ultrafiltration flow is verified. If, as in the illustrated case, the variation in flow rate ΔUFR is less than 3 ml/min, the setting sequence is considered to be concluded ("END" in FIG. 6) and the final TMP value reached (i.e. $TMP_4$ in FIG. 6) is imposed as set value. Otherwise, a new TMP increase is imposed, which can be again of 20 mmHg or can be a function of the variation measured ΔUFR in ultrafiltration flow UFR.

Figure 7:
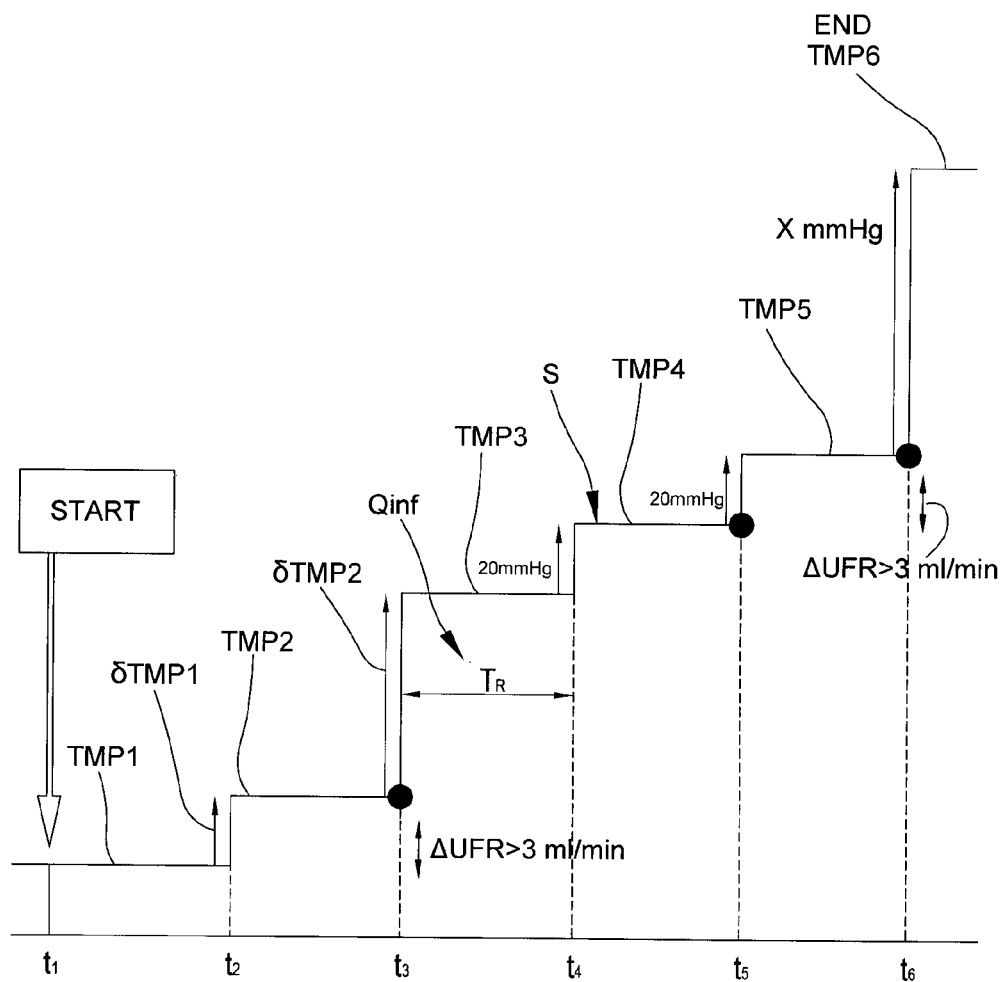
FIG. 7 is a time chart showing the progression of the transmembrane pressure TMP during a further setting sequence of the TMP, in an aspect of the invention.

FIG. 7 illustrates a situation in which the above-described steps are repeated up to reaching pressure $TMP_3$; thereafter, the setting sequence can comprise the TMP variation in one or two steps of predetermined entity with the aim of enabling stabilisation of the control system. The TMP variation or variations are kept lower than or equal to a relatively low value, for example 20 mmHg. For example, FIG. 7 shows a stabilising step, denotes by s. After a further time interval $t_4$-$t_5$, the sequence repeats the previously-described steps with reference to intervals from $t_2$ to $t_4$. In other words, at instant $t_5$, a pressure increment of 20 mmHg is imposed on the value of the TMP passing to a set value $TMP_5$ with a consequent activating of the ultrafiltration pump 13 and the infusion pump 16 (or at least one of the pumps 16a, 16b in the case of FIG. 2) such as to balance the effect of the greater ultrafiltration. If, as in FIG. 7, in interval $t_5$-$t_6$, the variation ΔUFR in ultrafiltration flow rate UFR is above 3 ml/min, for example 12 ml/min, the successive increment of the TMP set value is imposed at greater than 20 mmHg and, in the illustrated example, at 60 mmHg. In response to the new set value of TMP ($TMP_6$), the control unit also commands acceleration of the infusion pump such as to balance the effect of the greater ultrafiltration, according to one of the above-described control strategies. Then, a new TMP increase of 20 mmHg will be imposed and after a further interval T, the increase in the ultrafiltration flow rate ΔUFR will be verified. If in response the UFR varies by a value ΔUFR that is lower than 3 ml/min, the setting sequence is considered to be concluded. Otherwise, the described process is newly reiterated.

In general, the sequence comprises that at the start of the setting sequence a TMP increase with a predetermined value is imposed, which can be the same or can vary during treatment, but is known a priori and is normally relatively small, for example 20 mmHg. Increases after the first ($\delta TMP_{n+1}$) are either stabilising increases as described above, and therefore also of 20 mmHg or known and relatively small values, or TMP values calculated in accordance with the measured or estimated ultrafiltration variation value ΔUFR corresponding to the rise in immediately-preceding transmembrane pressure ($\delta TMP_n$), or rises in TMP that are always constant and of known amplitude a priori.

The preceding stages are repeated up to when, following a pressure step, the variation in ultrafiltration flow rate satisfies the end condition of the sequence: at this point, the control unit is configured such as to command the regulating device 20, setting, as operating transmembrane pressure, the last pressure at which the value of the control parameter is less than the value of the respective reference value.

If during the performing of the transmembrane setting sequence there is a modification in the weight loss rate due to the intervening of the control procedure (this can happen as the control procedure is repeated much more frequently than with the setting sequence), the setting sequence involves two actions. Firstly the variation in the ultrafiltration flow rate, if estimated as a function of the variation in the infusion rate, takes account of any variation in the weight loss rate, i.e. in each time interval $t_n$-$t_{n+1}$ (see FIGS. 6 and 7 for example) the variation ΔUFR is calculated as $\Delta Q_{INF}$+ΔWLR.

Further, the control unit 15 can be programmed such that during the setting sequence, following each command for increase of the transmembrane pressure, a time transitory $T_r$ is included (step 205 in FIG. 5) before performing a successive transmembrane pressure increase that is sufficiently long and generally of non-uniform duration. The control unit 15 is further predisposed to verify (step 206 in FIG. 5) if between an increase in pressure and the next, there has been a variation in weight loss rate ΔWLR imposed by the control procedure and, if the response is affirmative, the duration of the time transitory $T_r$ is prolonged such that at least one predetermined auxiliary time delay (step 207), for example 50 seconds, passes from the previous variation in weight loss rate.

During step 206 other verifications can also be made, such as a verification of any infusion stop and/or eventual flushing of one or more filter units which in any case would cause introduction of the auxiliary delay. Note that in all cases the auxiliary delay has a shorter duration than that of the period between a control procedure and a next.

In an aspect of the invention, the control unit can also be predisposed to calculate the time transitory $T_r$ in accordance with the increase in pressure between a transmembrane pressure $TMP_n$ and a next $TMP_{n+1}$ (prolonging $T_r$ in line if the TMP variation is greater) and/or as a function of the variation in weight loss rate ΔWLR imposed by the control procedure between a pressure increase and a next increase.

Thanks to this delay $T_r$, the control unit 15 compares the value of the variation in ultrafiltration flow ΔUFR with a respect reference value $\Delta UFR_{ref}$ only after the time transitory $T_r$ has passed, with the aim of enabling a stabilisation of the value of the ultrafiltration flow variation.

In a more detailed description of the calculation of the specific TMP steps, the control unit is configured (in the hypothesis in which $\Delta UFR_1 > \Delta UFR_{ref}$) such as to calculate the second increase $\delta TMP_2$ as a function of the value $\Delta UFR_1$ corresponding to the first increase $\delta TMP_1$, for example as a linear function of the $\Delta UFR_1$ value corresponding to the first increase $\delta TMP_1$ using the formula:

$$\delta TMP_2 = \Delta UFR_1 \cdot (K)$$

where:

K is the relation between the value of the first transmembrane pressure increase $\delta TMP_1$ and a correction factor, $\Delta UFR_1$ is the value for example of the variation in flow rate of the ultrafiltration pump 13 corresponding to the first increase in transmembrane pressure $\delta TMP_1$.

The value of $\delta TMP_1$ is predetermined and can be comprised between 10 and 30 mmHg (for example 20 mmHg).

The value of the correction factor can be determined in various ways: for example the value of the correction factor can be of a fixed amount and be greater than or equal to, preferably greater than, the reference parameter $\Delta UFR_{ref}$. In a second example, the control parameter value can be calculated as a function of $\Delta UFR_{ref}$ and for example can be expressed by the function $\Delta UFR_{ref}+1$. In this way, if following a first increase in pressure of 20 mmHg, a value of ΔUFR of 12 ml/min were to be measured, and if $\phi_{ref}=3$ ml/min, then the value of the second pressure increase would be given by the formula:

$$\delta TMP_2 = (12 \text{ ml/min}) \cdot (20 \text{ mmHg}/4 \text{ ml/min}) = 60 \text{ mmHg}$$

To prevent excessive pressure hikes, the control unit is configured such as to verify that each pressure increase is less than a maximum safety value, for example 100 mmHg. The maximum safety value could be programmable by the user or be set automatically by the control unit. In the last case the control unit can also be programmed to set a different maximum safety value in accordance with the type of treatment unit installed on the apparatus 1.

As has been mentioned, the described sequence can be manually or automatically activated. For example, the apparatus 1 can comprise at least one user interface 22, connected to the control unit and having at least one manual activating unit of the sequence. For example, if the interface is of the type having a touch screen, the activation unit can comprise a part of the screen on which the user can act by pressure in order to initiate the TMP setting sequence and the control procedure. The control unit is programmed to receive a start command of the sequence and/or of the procedure following the action exerted on the manual activation element. It is also possible to deactivate the setting sequence and/or the control procedure manually by acting on it or on a further element of the user interface 22.

Alternatively, or additionally, the control unit 15 is programmed to automatically start the setting sequence and/or the control procedure. In this case, the control unit is programmed to cyclically repeat the control procedure, in brief intervals of for example one minute, and to automatically activate a first setting sequence after a brief time interval from the start of treatment.

The control unit can also be configured such as to measure a time that has passed since the end of the first sequence, and to automatically activate a second sequence after a second period of time has passed since the end of the first sequence.

Figure 8:
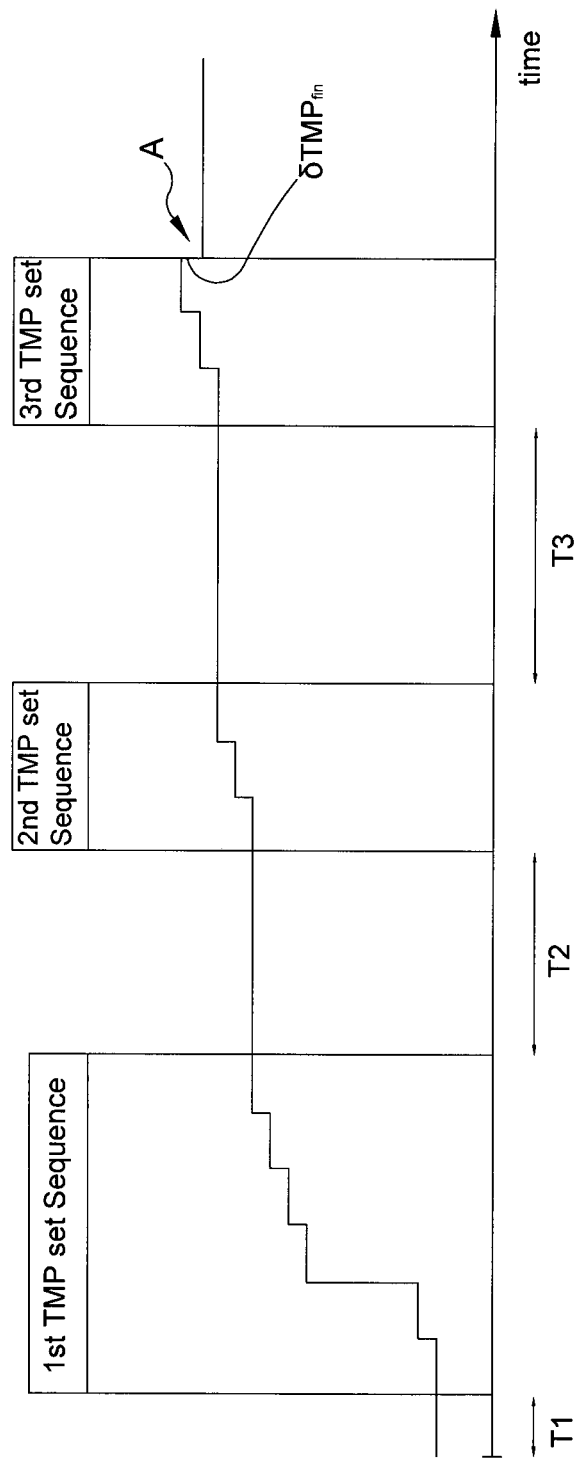
FIG. 8 is a time chart relating to a plurality of successive TMP setting sequences, in an aspect of the invention.
Figure 9:
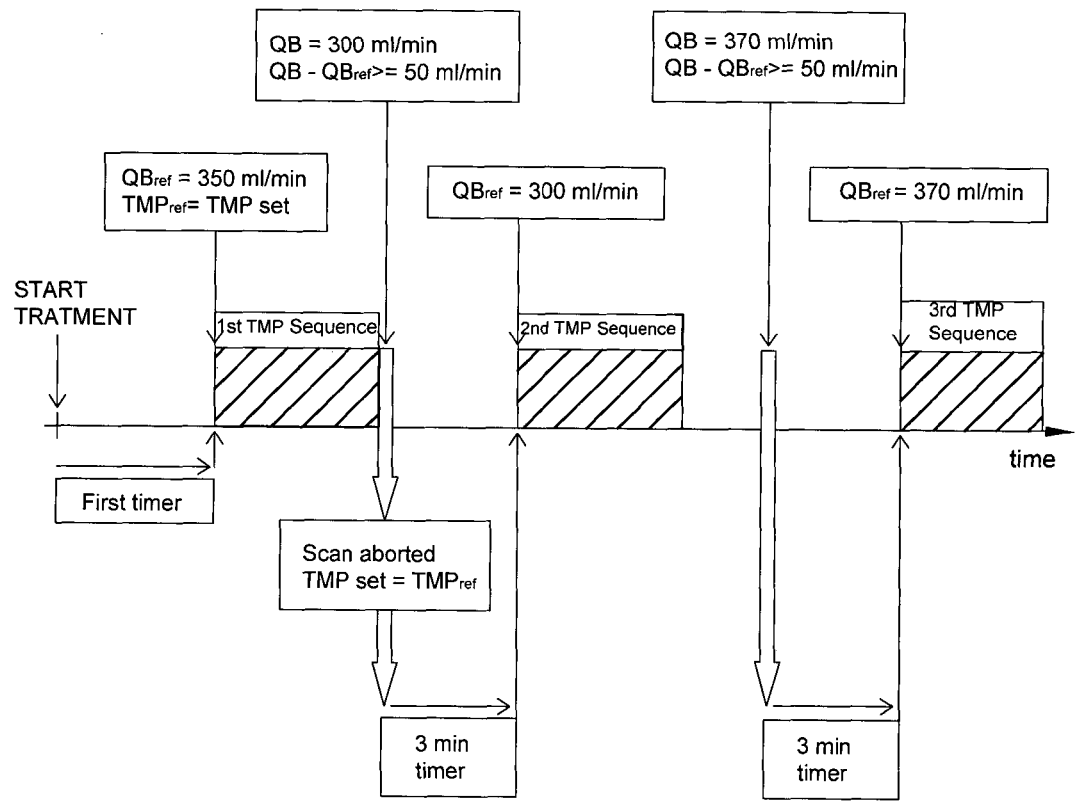
FIG. 9 is a time chart relating to a plurality of TMP setting sequences, in the presence of setting variations in the blood flow rate.

In the example of FIG. 8, a first setting sequence is activated after a time interval $T_1$ since start of treatment, the activation of a second setting sequence after a time interval $T_2$ after the end of the first sequence, and finally activating of a third sequence after a time interval $T_3$ following the end of the second sequence. According to the type of requirement, such as for example duration of the treatment, type of treatment unit, and more besides, it is possible to have a different number (two, three or more) of sequences during the treatment period.

During the three sequences the control unit is also performing the control procedure 100 in parallel, such as to reach the desired objectives of weight loss and plasma sodium concentration in the patient without causing problems of hypovolemia.

The duration of the time intervals between consecutive sequences is optionally not uniform: for example the duration of each time interval following the first ($T_2$, $T_3$, . . . $T_n$) is greater than the duration of a time interval that precedes it.

The control unit can also be programmed to perform, following a setting sequence, a step of moderating the TMP setting value. In particular, following the second or the third or the last setting sequence, a step of moderating (denoted by A in FIG. 8) is included, which comprises lowering the TMP value determined thanks to the setting sequence by a predetermined amount δTMP with the aim of preventing the plateau zone of the TMP/UF curve from being reached. FIG. 8 shows a succession of three setting sequences in which, following the third and final sequence, a reduction in TMP by a value δTMP is included, for example 20 mmHg.

As can be seen in FIGS. 1 and 2, the apparatus 1 comprises at least one blood pump 21, operatively connected to the control unit 15 and operating at the removal line 6 or the return line 7. From the constructional point of view, the blood pump can be a peristaltic pump. The control unit 15 can also be programmed to detect a variation in the set value of the blood pump, which for example can be altered via the user interface 22. Normally, the value of the blood pump is imposed at the start of treatment and maintained constant during treatment. If however the blood flow rate should be changed, the control unit 15 can be programmed to:
  detect the change,
  verify whether the change is of a greater entity than a predetermined threshold,
  interrupt the setting sequence (whether manually started or automatic).

For example, the control unit 15 interrupts the sequence if a variation is verified that is greater for example than 50 ml/min: this is because the variation in the blood flow leads to a variation in TMP though the other operating conditions remain unaltered.

If the blood flow rate is reduced during the performing of the setting sequence, for example if the blood flow rate is reduced by more than for example 50 ml/min, the control unit can be programmed to:
  interrupt the setting sequence,
  impose a new TMP start value from which to begin the new setting sequence, whether the new sequence initiates automatically or by manual on/off command;
  if an automatic procedure is imposed, automatically start the sequence after a minimum time (for example three minutes) from the setting of the new blood flow rate;
  if a manual procedure is imposed, send a user message to the user interface 22 which invites the user to start the sequence after a minimum time from the setting of the new blood flow rate.

If the blood flow rate is reduced in an interval between two consecutive setting sequences, the control unit can be programmed to:
  set a new TMP start value from which to begin a new setting sequence, whether the new sequence initiates automatically or by manual on/off command;
  if an automatic procedure is imposed, automatically start the sequence after a minimum time (for example three minutes) from the imposing of the new blood flow rate;
  if a manual procedure is imposed, send a user message to the user interface 22 which invites the user to start the sequence after a minimum time from the setting of the new blood flow rate.

If the blood flow rate is increased during the performing of the setting sequence, for example if the blood flow rate is increased by more than 50 ml/min, the control unit 15 can be programmed to:
  interrupt the setting sequence,
  impose a new start TMP value from which to begin the new setting sequence, whether the new sequence initiates automatically or by manual on/off command; if an increase of TMP has been performed with respect to a start treatment value, the new TMP value is the one obtained by reducing the currently-set TMP by a predetermined step, for example by 20 mmHg,
  if an automatic procedure is imposed, automatically start the sequence after a minimum time (for example three minutes) from the setting of the new blood flow rate;
  if a manual procedure is imposed, send a user message to the user interface 22 which invites the user to start the sequence after a minimum time from the setting of the new blood flow rate.

If the blood flow rate is increased in an interval between two consecutive setting sequences, for example if the blood rate flow is increased by more than 50 ml/min, the control unit can be programmed to:
  if an automatic procedure is imposed, automatically start the sequence after a minimum time (for example three minutes) from the setting of the new blood flow rate;
  if a manual procedure is imposed, send a user message to the user interface 22 which invites the user to start the sequence after a minimum time from the setting of the new blood flow rate.

The invention claimed is:

1. An apparatus for extracorporeal blood treatment comprising:
  at least a treatment unit having at least a first chamber and at least a second chamber separated from one another by a semipermeable membrane;
  at least a blood removal line connected to an inlet port of the first chamber and predisposed to remove blood from a patient,
  at least a blood return line connected to an outlet port of the first chamber and predisposed to return treated blood to the patient, the blood removal line, the blood return line and the first chamber being part of an extracorporeal blood circuit;
  at least an infusion line of a replacement fluid connected to the extracorporeal circuit or directly connectable to the patient;
  a dialysis line connected to an inlet port to the second chamber;
  at least a fluid evacuation line connected to an outlet port of the second chamber;
  a first sensor configured to obtain data regarding a first parameter relating to a blood volume (BV %) of the patient;
  a second sensor configured to obtain data regarding a second parameter relating to at least one of: an ultrafiltration flow rate (UFR) through the semipermeable membrane, a weight loss rate (WLR) of the patient, and an accumulated weight loss (WL) of the patient;

a third sensor configured to obtain data regarding a third parameter relating to at least one of: a conductivity of a liquid in the dialysis line or the infusion line (Cd), or a concentration in a predetermined substance of the liquid in the dialysis line or in the infusion line (Na);

a fourth sensor configured to obtain data of a fourth parameter relating to at least one of: an infusion flow rate ($Q_{INF}$) of the replacement fluid in the infusion line, and a transmembrane pressure (TMP) between the first chamber and the second chamber;

a control unit in communication with the sensors and programmed to perform a control procedure comprising:

receiving, from the sensors, the data and determining values of the first parameter (BV $\%_{mes(t)}$), the second parameter ($UFR_{mes(t)}$; $WLR_{mes(t)}$, or $WL_{mes(t)}$), the third parameter ($Cd_{mes(t)}$ or $Na_{mes(t)}$) and the fourth parameter ($Q_{INFmes(t)}$ or $TMP_{mes(t)}$);

on the basis of said determined values and of prescribed values for a variation in blood volume (BV $\%_{target}$), a target weight loss ($WL_{target}$), plasma conductivity or concentration in the predetermined substance ($C_{target}$, $Na_{target}$), and an infusion volume ($V_{INFtarget}$) to be reached in the patient or a transmembrane pressure ($TMP_{target}$) to be reached during a predetermined treatment time, calculating control values corresponding to a control instant (t), wherein the control values include: (i) a conductivity or sodium concentration value ($Cd_{(t)}$; $Na_{(t)}$) of the liquid flowing through the dialysis line or the infusion line; (ii) a weight loss rate value ($WLR_{(t)}$), and (iii) at least one of an infusion rate value ($Q_{INF(t)}$) and a transmembrane pressure value ($TMP_{(t)}$), and imposing on the apparatus the control values during a time interval ($\Delta t$) following the control instant (t).

2. The apparatus of claim 1, wherein the control values are calculated on a basis of:

measured values where the fourth parameter is the infusion rate, and prescribed values of the blood volume variation (BV $\%_{target}$), of the weight loss ($WL_{target}$), of the plasma conductivity or concentration of the predetermined substance ($C_{target}$, $Na_{target}$), and of the infusion volume ($V_{INFtarget}$) to be reached in the patient in a predetermined treatment time.

3. The apparatus of claim 1, wherein the control values are calculated on the basis of:

measured values where the fourth parameter is the transmembrane pressure and prescribed values of the blood volume variation (BV $\%_{target}$), of the weight loss ($WL_{target}$), of the plasma conductivity or concentration of the predetermined substance ($C_{target}$) to be reached in the patient in a predetermined treatment time, and of the transmembrane pressure ($TMP_{target}$) predetermined or calculated to be followed during the predetermined treatment time.

4. The apparatus of claim 1, wherein the control values are calculated also on the basis of a prescribed value of a volume to be infused in the patient ($V_{INFtarget}$) by end of treatment.

5. The apparatus of claim 1, wherein the control values are calculated also on the basis of a prescribed flow rate of a volume to be infused in the patient ($Q_{INFtarget}$) during the treatment.

6. The apparatus of claim 1, comprising:

a first regulating device for regulating an ultrafiltration rate or a transmembrane pressure between the first and the second chamber of the treatment unit, the first regulating device being connected to the control unit and being active on at least one of the extracorporeal blood circuit and the fluid evacuation line, a second regulating device for regulating a composition of the dialysis liquid and/or the replacement liquid, the second regulating device being connected to the control unit and being active on the dialysis line and/or on the infusion line for regulating the conductivity or concentration in a predetermined substance (Cd, Na) of the liquid in the dialysis line and/or the infusion line;

and wherein the step of imposing the control values during the procedure comprises:

commanding the second regulating device to impose the control value relating to the conductivity or concentration in a predetermined substance ($Cd_{(t)}$, $Na_{(t)}$) on the liquid crossing the dialysis line and/or the infusion line; and commanding the first regulating device to impose the control value relating to the weight loss rate ($WLR_{(t)}$).

7. The apparatus of claim 6, comprising at least an infusion pump active on the infusion line and connected to the control unit for causing an infusion liquid flow along the line and wherein the control unit is configured to control the infusion pump and the first regulating device to impose:

both the control value relating to the weight loss rate ($WLR_{(t)}$) and the control value relating to the infusion flow rate ($Q_{INF(t)}$).

8. The apparatus of claim 6, comprising at least an infusion pump active on the infusion line and connected to the control unit for causing an infusion liquid flow along the line and wherein the control unit is configured to control the infusion pump and the first regulating device to impose:

both the control value relating to the weight loss rate ($WLR_{(t)}$) and the transmembrane pressure ($TMP_{(t)}$).

9. The apparatus of claim 6, wherein the control unit is configured to command the second regulating device in order to impose the control parameter relating to the conductivity or the concentration in a predetermined substance ($Cd_{(t)}$, $Na_{(t)}$) both to the liquid crossing the dialysis line and the liquid crossing the infusion line.

10. The apparatus of claim 1, wherein the control procedure uses a mathematical model (M), representing kinetics of the solutes in a distribution volume in the patient, in order to determine an equivalent sodium concentration value ($Na_{eq(t)}$) at the control instant (t), the model being memorised in a memory associated to the control unit, the control unit being configured to apply the following values in inlet to the mathematical model:

a value of the equivalent sodium concentration relative to a preceding control instant ($Na_{eq(t-\Delta t)}$), a control value of the conductivity or sodium concentration of the dialysis liquid at a preceding control instant ($Cd_{(t-\Delta t)}$; $Na_{(t-\Delta t)}$), at least a selected value from a group comprising: a control value relating to the ultrafiltration flow at a preceding control instant ($UFR_{(t-\Delta t)}$), a control value relating to the weight loss rate at the preceding control instant ($WLR_{(t-\Delta t)}$), an accumulated weight loss up to a preceding control instant ($WL_{(t-\Delta t)}$), an accumulated weight loss value at control instant ($WL_{(t)}$), a total convective and diffusive clearance value measured at the control instant ($Cl_{mes(t)}$) or an estimated total convective and diffusive clearance parameter ($Cl_{mes(t)}$), for example based on:

a current measured value of the infusion flow rate ($Q_{INFmes(t)}$) and of one from among a current measured value of blood flow ($Q_{Bmes(t)}$) and a current diffusive clearance value ($Cl_{diff(t)}$), or preceding values assumed by the Clearance;

a reference value relating to a distribution volume (V) of solutes in the patient;

and to receive in output from the mathematical model a value of an equivalent sodium concentration ($Na_{eq(t)}$) at the control instant (t), wherein the mathematical model is representative of a kinetics of the solutes in a distribution volume in the patient, optionally according to a single-compartment model, wherein by equivalent sodium concentration at instant t ($Na_{eq(t)}$) is intended the constant sodium concentration in the dialysis liquid which, if it were applied at the start of treatment up to a certain instant (t), would lead to the same plasma sodium concentration in the patient as is obtained at the same instant (t) with the variation in sodium concentration or conductivity imposed by the control procedure up to time (t), and wherein the control procedure comprises also using the equivalent sodium concentration value at the instant t ($Na_{eq(t)}$) for the determination of the control values.

11. The apparatus of claim 1, wherein the prescribed substance is sodium and wherein the control procedure comprises following sub-steps:

receiving the prescribed values of the blood volume variation (BV $\%_{target}$), the weight loss ($WL_{target}$) and the plasma conductivity or sodium concentration ($C_{target}$, $Na_{target}$) to be reached at end of treatment;

receiving a treatment time value (T);

determining, on the basis of the prescribed values and the treatment time value (T) respective target profiles which describe the desired temporal progression of the blood volume variation (BV $\%_{target(t)}$), of the weight loss or the weight loss rate ($WL_{target(t)}$, $WLR_{target(t)}$), and of the equivalent sodium concentration ($Na_{eq-target(t)}$).

12. The apparatus of claim 11, wherein the control comprises sub-steps of:

determining at least a first error parameter ($ERR\_BV\_UF_{(t)}$) on the basis of:

the difference between the measured value of the first parameter (BV $\%_{mes(t)}$) at the control instant (t) and a corresponding value on the target profile relating to the variation in blood volume over the time (BV $\%_{target(t)}$) and the difference between a measured value of the weight loss or the weight loss rate ($WL_{mes(t)}$; $WLR_{mes(t)}$) at the control instant (t) and a corresponding value given by the target profile relating to the weight loss or the weight loss rate ($WL_{target(t)}$; $WLR_{target(t)}$) over the time; and determining at least a second error parameter ($ERR\_BV\_Na_{(t)}$) on the basis of:

the difference between the value of the equivalent sodium concentration ($Na_{eq(t)}$ at the control instant (t) and a corresponding value on the target profile relating to the variation over the time of the equivalent sodium concentration ($Na_{eg-target(t)}$ and the difference between the measured value of the first parameter (BV $\%_{mes(t)}$) at the control instant t and the corresponding value on the target profile on variation of the blood volume in time (BV $\%_{target(t)}$).

13. The apparatus of claim 12, wherein:

a conductivity or sodium concentration value ($Cd_{(t)}$; $Na_{(t)}$) to be imposed on the liquid crossing the dialysis line and/or the infusion line is calculated on the basis of the second error parameter ($ERR\_BV\_Na_{(t)}$) and according to the value of conductivity or sodium concentration ($Cd_{(t-\Delta t)}$, $Na_{(t-\Delta t)}$) relating to the preceding control instant; and wherein the control flow value to be imposed on the weight loss rate ($WLR_{(t)}$) is calculated on the basis of the error parameter ($ERR\_BV\_UF_{(t)}$ and on the basis of the ultrafiltration flow rate value ($UFR_{(t-\Delta t)}$) relating to the preceding control instant.

14. The apparatus of claim 1, wherein the control unit is configured to:

compare the measured values of the first parameter (BV $\%_{mes(t)}$) with a reference threshold, verify whether the measured value of the first parameter falls below the threshold, and command the infusion of a bolus of a predetermined volume of replacement liquid across the infusion line if the verification gives a positive result.

15. The apparatus of claim 14, wherein the commanding of the infusion of the bolus comprises imposing a predetermined flow rate for a predetermined administration time on the infusion pump.

16. The apparatus of claim 15, wherein the control unit is configured to impose, during the administration of the bolus, an ultrafiltration flow rate of zero.

17. The apparatus of claim 15, wherein the commanding of the infusion of the bolus comprises commanding, during administration of the bolus, the second regulating device of the liquid composition to impose a predetermined value on the conductivity or concentration in the prescribed substance ($Cd_{(t)}$, $Na_{(t)}$) of the liquid in the infusion line.

18. The apparatus of claim 14, wherein the commanding of the infusion of the bolus comprises commanding, during administration of the bolus, the second regulating device of the liquid composition to impose a predetermined value on the conductivity or concentration in the prescribed substance ($Cd_{(t)}$, $Na_{(t)}$) of the liquid in the infusion line.

19. The apparatus of claim 1, wherein the commanding of the infusion of the bolus comprises commanding, during administration of the bolus, the second regulating device of the liquid composition to impose a predetermined value on the conductivity or concentration in the prescribed substance ($Cd_{(t)}$, $Na_{(t)}$) of the liquid in the infusion line.

20. A system for extracorporeal blood treatment comprising:

a blood treatment unit having a first chamber, a second chamber and a semipermeable membrane separating the first chamber and the second chamber;

a blood removal line connected to an inlet port of the first chamber and connectable to a vascular system of a patient, a blood return line connected to an outlet port of the first chamber and connectable to the vascular system, wherein the blood removal line, the blood return line and the first chamber comprise an extracorporeal blood circuit;

an infusion line connectable to a source of a replacement fluid and to the extracorporeal circuit or directly to the vascular system;

a dialysis line connected to inlet to the second chamber;

a fluid evacuation line connected to an outlet port of the second chamber;

a first sensor obtaining data regarding a first parameter indicating to a blood volume (BV %) of the patient;

a second sensor obtaining data regarding a second parameter indicating at least one of: an ultrafiltration flow rate (UFR) through the semipermeable membrane, a weight loss rate (WLR) of the patient, and an accumulated weight loss (WL) of the patient;

a third sensor obtaining data regarding a third parameter indicating at least one of: a conductivity (Cd) of a liquid in the dialysis line or the infusion line, and a concentration (Na) of a predetermined substance in the liquid in the dialysis line or the infusion line;

a fourth sensor obtaining data regarding a fourth parameter which is selected in the group of: an infusion flow rate ($Q_{INF}$) of the replacement fluid in the infusion line, a transmembrane pressure (TMP) between the first chamber and the second chamber;

a control unit including a processor and a non-transitory storage medium including instructions which when executed by the processor cause the control unit to:

receive from the first, second, third and fourth sensors the data regarding the first, second, third and fourth parameters;

on the basis of said data regarding the first, second, third and fourth parameters, and prescribed values for a variation in blood volume (BV $\%_{target}$), a target weight loss ($WL_{target}$) plasma conductivity or concentration in the predetermined substance ($C_{target}$, $Na_{target}$), and an infusion volume ($V_{INFtarget}$) to be reached in the patient or a transmembrane pressure ($TMP_{target}$) to be reached during a predetermined treatment time, calculating control values corresponding to a control instant (t), wherein the control values include: (i) a conductivity or sodium concentration value ($Cd_{(t)}$; $Na_{(t)}$) of the liquid flowing through the dialysis line or the infusion line; (ii) a weight loss rate value ($WLR_{(t)}$), and (iii) at least one of an infusion rate value ($Q_{INF(t)}$) and a transmembrane pressure value ($TMP_{(t)}$), and imposing on the system the control values during a time interval ($\Delta t$) following the control instant (t).

* * * * *